United States Patent

Ohuchi et al.

[11] Patent Number: 5,753,673
[45] Date of Patent: May 19, 1998

[54] QUINOLINECARBOXYLIC ACID DERIVATIVES

[75] Inventors: Yutaka Ohuchi; Masaji Suzuki; Hajime Asanuma; Sadakazu Yokomori; Katsuo Hatayama, all of Tokyo, Japan

[73] Assignee: Taisho Pharmaceutical Co., Ltd., Tokyo, Japan

[21] Appl. No.: 578,532

[22] PCT Filed: May 18, 1995

[86] PCT No.: PCT/JP95/00954

§ 371 Date: Jan. 18, 1996

§ 102(e) Date: Jan. 18, 1996

[87] PCT Pub. No.: WO95/31455

PCT Pub. Date: Nov. 23, 1995

[30] Foreign Application Priority Data

May 18, 1994  [JP]  Japan ................... 6-103177

[51] Int. Cl.$^6$ .............. A61K 31/46; C07D 451/06; C07D 451/04
[52] U.S. Cl. .............. 514/304; 514/235.2; 544/128; 546/126
[58] Field of Search .............. 546/126; 544/128; 514/235.2, 304

[56] References Cited

FOREIGN PATENT DOCUMENTS

| | | |
|---|---|---|
| 49086/A | 10/1990 | Australia . |
| 0 458 636 | 11/1991 | European Pat. Off. . |
| WO 94/12497 | 6/1994 | WIPO . |

*Primary Examiner*—Patricia L. Morris
*Attorney, Agent, or Firm*—Oblon, Spivak, McClelland, Maier & Neustadt, P.C.

[57] ABSTRACT

Quinolinecarboxylic acid derivatives represented by the following formula:

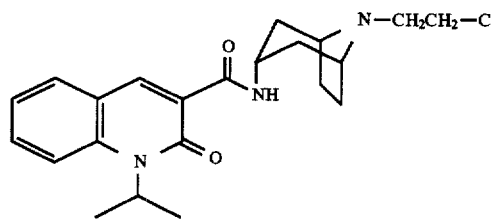

wherein C is hydroxymethyl, methoxy, ethoxy or morpholinyl, or pharmaceutically acceptable salts thereof exhibit a potent action for stimulating a serotonin 4 receptor. The compounds exhibit an action of enhancing the gastrointestinal motor function to improve the gastrointestinal conditions such as heartburn, anorexia, bowel pain, abdominal distension, etc., accompanied by chronic gastritis, diabetes mellitus or postoperative gastroparesis, and are thus effective for the treatment of gastro-esophagal reflux, intestinal pseudo-obstruction and constipation.

6 Claims, 1 Drawing Sheet

QUINOLINECARBOXYLIC ACID DERIVATIVES

TECHNICAL FIELD

The present invention relates to a quinolinecarboxylic acid derivative. More particularly, the present invention relates to a novel quinolinecarboxylic acid derivative, which has an action for stimulating a serotonin 4 receptor. The present invention also relates to a pharmaceutical use of such a quinolinecarboxylic acid derivative and an intermediate thereof.

BACKGROUND ART

Serotonin is a neurotransmitter which is widely distributed in human and has a remarkable variety of physiological effects. It is hitherto known that serotonin receptors include three subtypes of serotonin 1 receptor, serotonin 2 receptor and serotonin 3 receptor. In addition to these receptors, the existence of serotonin 4 receptor was reported by DUMUIS, A., et al., see Molecular Pharmacology, 34, 880, 1988.

The Serotonin 4 receptor forms a conjugate with a G(Gs) protein to accelerate an adenylate cyclase activity, cf., DUMUIS, A., et al., supra. It is suggested that the receptor is located prejunctionally and promotes the release of acetylcholine through cyclic AMP-dependent block of K channel see RIZZI, C. A. et al., J. Pharmacol. Exp. Ther., 1992, 412–419 (1992).

In the central nervous system, a localization of the serotonin 4 receptor is observed on a high level in the striatum, hippocampus, substantia nigra, olfactory tubercle, etc. but with low concentrations in the cerebral cortex, see GROSSMAN, C. J. et al., Br. J. Pharmacol., 109, 618–624 (1993). There are some reports on smooth muscle relaxation (REEVES, K. Y. et al., Br. J. Pharmacol., 103, 1067–1072 (1991)) and on the cardiovascular effects in both human and pig (BOM, A. H. et al., Br. J. Pharmacol., 93, 663–671 (1988); VILLALON, C. M., et al., ibid., 100, 665–667 (1990); and EGLEN, R. M. et al., ibid., 101, 513–520 (1990)).

In the gut, it is reported that the various actions through the serotonin 4 receptors are observed to show cholinergic nerve-mediating contraction in the guinea pig ileum and in the proximal colon (KAUMANN, A. J. et al., Br. J. Pharmacol., 100, 879–885 (1990) and ELSWOOD, C. L. et al., Eur. J. Pharmacol., 196, 149–155 (1991)), a potentiation of electrical field stimulation in the guinea pig ileum (CRAIG, D. A. et al., Br. J. Pharmacol. Exp. Ther., 252, 1378–1386 (1990)), an induction of chloride secretion in rat distal colon (BUNCE, K. T. et al., Br. J. Pharmacol., 102, 811–816 (1991).

These results suggest that the serotonin 4 receptor present in the gut would take a part in the induction and maintenance of gastrointestinal motility and serotonin 4 receptor stimulants would activate the gastrointestinal motor function to exhibit the action of treating and improving the gastrointestinal dysfunctions or conditions accompanied by motility failure. In fact, cisapride and renzapride, which are effective for stimulating the serotonin 4 receptor, are reported to accelerate the gastrointestinal motor function and improve the gastrointestinal conditions such as heartburn, anorexia, bowel pain, abdominal distension, etc., accompanied by chronic gastritis, diabetes mellitus or postoperative gastroparesis, and are thus effective for the treatment of gastro-esophagal reflux, intestinal pseudo-obstruction and constipation, see TALLEY, N. J., Alimentary Pharmacology and Therapeutics, 6, 273 (1992).

As heterocyclic compounds which possess an activity of antagonizing or stimulating serotonin receptors, Japanese Patent Application Laid-Open No. 4-226980 (European Patent No. 0458636A1) discloses quinoline derivatives which antagonize serotonin 3 receptor. Serotonin 3 receptor antagonists are used to prevent nausea or vomiting induced by antitumor agents or upon radiotherapy. In addition, these antagonists suppress the gastrointestinal motility in the descending gut and are thus considered to be effective for diarrhea-predominant irritable bowel syndrome.

On the other hand, Japanese Patent Application Laid-Open No. 3-197462 (U.S. Pat. No. 5,106,851) discloses quinazolinecarboxylic acid derivatives as heterocyclic compounds that are effective for the treatment of gastrointestinal disorders.

In the clinical field of gastrointestinal disorders, pirenzepine has been made available as an anti-secretory and anti-ulcer agent which functions as a muscarine 1 receptor antagonist. This is because muscarine 2 (or muscarine 3) is present in smooth muscles as the muscarine receptor so that its antagonizing action against the gastrointestinal motility is slight. However, in vitro studies indicate that the muscarine 1 receptor antagonist does not act on any of the gastrointestinal motility but exhibits a slightly inhibitory action. This is because the muscarine 1 receptor exists on the myenteric ganglia in the gut and considered to be participated in promoting neuro-transmission. It is therefore considered that the serotonin 3 receptor antagonists and muscarine 1 receptor antagonists would be drugs expected to exert the effect based on their function-inhibiting activity, whereas the serotonin 4 receptor stimulants are expected to show the function-promoting activity over the entire gastrointestinal tract.

As stated above, there is no report on such quinoline compounds having an excellent antagonizing or stimulating activity particularly on the serotonin 4 receptor.

Accordingly, an object of the present invention is to provide a novel quinolinecarboxylic acid derivative having a potent stimulating activity especially on the serotonin 4 receptor and a pharmaceutical use thereof.

DISCLOSURE OF INVENTION

The present inventors have made extensive studies to find a novel compound for stimulating a serotonin 4 receptor. As a result, it has been discovered that a certain quinolinecarboxylic acid derivative possesses a potent serotonin 4 receptor-stimulating activity. By further investigations based on the discovery, the present invention has been attained.

The present invention relates to a quinolinecarboxylic acid derivative represented by formula (A):

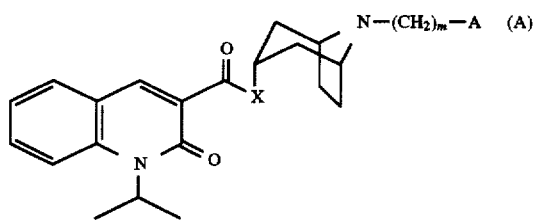

wherein:

X represents an oxygen atom or imino group;

m represents 0 or an integer of 1 to 6; and,

A represents an alkenyl group, an alkynyl group, a haloalkyl group, hydroxy group, an alkoxy group, an acyloxy group, an alkoxyalkoxy group, a mono- or di-alkylamino group, an alkylthio group, an alkylsulfinyl group, an alkylsulfonyl group, an arylsulfonyl group, an aryloxy group, morpholinyl group, piperidyl group, tetrahydropyranyl group, an alkoxycarbonyl group, carboxyl group, an alkanoyl group, cyano group or carbamoyl group; or a pharmaceutically acceptable salt thereof.

The present invention also relates to the quinolinecarboxylic acid derivative or a pharmaceutically acceptable salt thereof for use in a pharmaceutical composition.

The present invention further relates to use of the quinolinecarboxylic acid derivative or a pharmaceutically acceptable salt thereof for the preparation of a pharmaceutical composition for stimulating a serotonin 4 receptor.

The present invention further relates to a pharmaceutical composition for stimulating a serotonin 4 receptor which comprises as an effective ingredient the quinolinecarboxylic acid derivative or a pharmaceutically acceptable salt thereof.

The present invention also relates to a method for stimulating a serotonin 4 receptor which comprises administering to human an effective dose of the quinolinecarboxylic acid derivative or a pharmaceutically acceptable salt thereof.

The present invention further relates to a compound represented by formula (12):

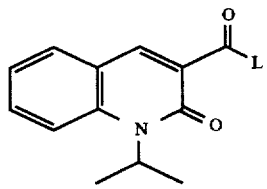
(12)

wherein L represents a halogen atom, an alkoxy group having 1 or 3 or more carbon atoms, an aryloxy group, an alkoxycarbonyloxy group, an acyloxy group, imidazolyl group or azide group, which is an intermediate for preparing the quinolinecarboxylic acid derivative or a pharmaceutically acceptable salt thereof.

The present invention further relates to a compound represented by formula (23):

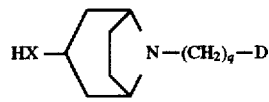
(23)

wherein X represents an oxygen atom or imino group; q represents an integer of 2 to 6; and D represents hydroxymethyl group, an alkoxy group having 2 to 6 carbon atoms or morpholinyl group, or a salt thereof, which is an intermediate for preparing the quinolinecarboxylic acid derivative or a pharmaceutically acceptable salt thereof.

BEST MODE FOR CARRYING OUT THE INVENTION

Figure 1:
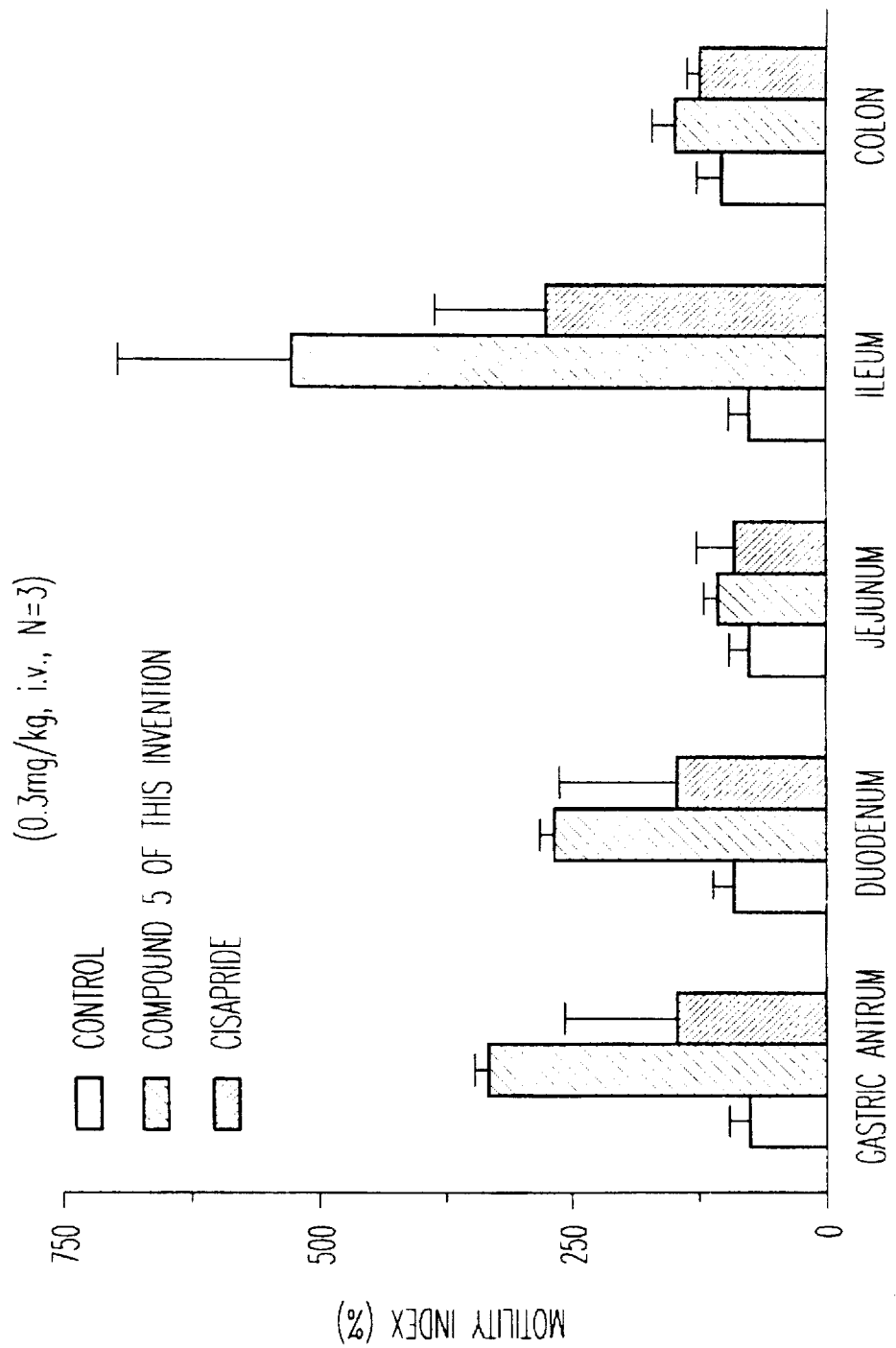
FIG. 1 is a graph showing the activity of the quinolinecarboxylic acid derivative of the present invention on the gastrointestinal motility in postprandial state in dog.

In the quinolinecarboxylic acid derivative represented by formula (A) above, examples of the group shown by A are given below. Specific examples of the alkenyl group include an alkenyl group having 2 to 6 carbon atoms such as vinyl, allyl, propenyl, 2-propenyl, butenyl, pentenyl and hexenyl. Specific examples of the alkynyl group include an alkynyl group having 2 to 6 carbon atoms such as ethynyl, propargyl, butynyl and pentynyl. Specific examples of the haloalkyl group include a haloalkyl group having 1 to 3 carbon atoms such as trifluoromethyl, trifluoroethyl and trichloromethyl. Specific examples of the alkoxy group include an alkoxy group having 1 to 6 carbon atoms such as methoxy, ethoxy, isopropoxy and t-butoxy. Specific examples of the acyloxy group include an acyloxy group having 2 to 8 carbon atoms such as acetyloxy, propanoyloxy, butanoyloxy and hexanoyloxy. Specific examples of the alkoxyalkoxy group are an alkoxyalkoxy group having 2 to 8 carbon atoms such as methoxymethoxy, 2-methoxyethoxy, 3-methoxypropoxy, 2-ethoxyethoxy, 3-ethoxypropoxy and 4-methoxybutoxy. Specific examples of the mono- or di-alkylamino group include a mono- or di-alkylamino group having 1 to 6 carbon atoms such as monomethylamino, dimethylamino, monoethylamino, diethylamino, monopropylamino and monobutylamino. Specific examples of the alkylthio group are an alkylthio group having 1 to 6 carbon atoms such as methylthio, ethylthio, butylthio, propylthio and hexylthio. Specific examples of the alkylsulfinyl group include an alkylsulfinyl group having 1 to 6 carbon atoms such as methylsulfinyl, ethylsulfinyl, butylsulfinyl and hexylsulfinyl. Specific examples of the alkylsulfonyl group are an alkylsulfonyl group having 1 to 6 carbon atoms such as methylsulfonyl, ethylsulfonyl, butylsulfonyl and hexylsulfonyl. Specific examples of the arylsulfonyl are an arylsulfonyl group having 6 to 12 carbon atoms such as phenylsulfonyl, tolylsulfonyl and naphthylsulfonyl. Specific examples of the aryloxy group are an aryloxy group having 6 to 12 carbon atoms such as phenoxy, tolyloxy and naphthyloxy. Specific examples of the alkoxycarbonyl group are an alkoxycarbonyl group having 2 to 7 carbon atoms such as methoxycarbonyl, ethoxycarbonyl, butoxycarbonyl and propoxycarbonyl. Specific examples of the alkanoyl group include an alkanoyl group having 2 to 8 carbon atoms such as methanoyl, ethanoyl, propanoyl, butanoyl and hexanoyl.

In the present invention, preferred are quinolinecarboxylic acid derivatives represented by formula (B):

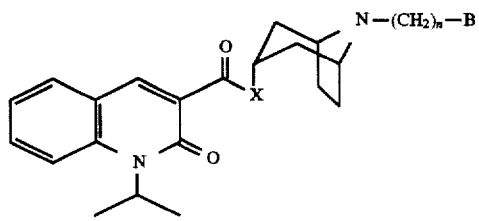

wherein X represents an oxygen atom or imino group; n represents an integer of 1 to 6; and Y represents hydroxy group, an alkoxy group, an alkanoyl group, an alkoxycarbonyl group or morpholinyl group, or pharmaceutically acceptable salts thereof.

In formula (B), preferred examples of the alkoxy group, the alkanoyl group and the alkoxycarbonyl group shown by group B are the same as those given for group A in formula (A).

Particularly preferred are quinolinecarboxylic acid derivatives represented by formula (C):

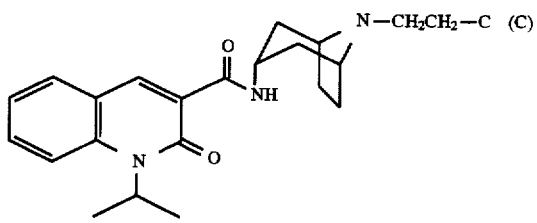

wherein Z represents hydroxymethyl, methoxy, ethoxy or morpholino group, or pharmaceutically acceptable salts thereof.

Preferred examples of the pharmaceutically acceptable salts of the compounds in accordance with the present invention are acid addition salts obtained by adding pharmacologically acceptable acids thereto.

Specific examples of the acid addition salts are acid addition salts with mineral acids such as hydrochloric acid, hydrobromic acid, hydroiodic acid, sulfuric acid, nitric acid or phosphoric acid; salts with organic acids such as acetic acid, citric acid, tartaric acid, maleic acid, succinic acid, fumaric acid, p-toluenesulfonic acid, benzenesulfonic acid or methanesulfonic acid.

The pharmaceutically acceptable salts may also be in the form of quaternary salt derivatives of the compounds shown by formula (A), which are represented by the following formula:

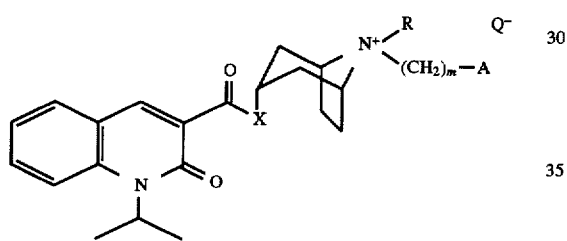

wherein X, A, R, m and Q have the same significance as defined above, and which may be obtained by reacting the compounds of formula (A) with compounds of formula (I):

R—Q  (I)

wherein R represents a lower alkyl group such as methyl, ethyl and propyl; and Q represents a halogen atom such as fluorine, chlorine and bromine, or tosylate or mesylate.

The compounds of the present invention represented by formula (A) can be produced, for example, by Preparation Scheme I or Preparation Scheme II shown below.

Preparation Scheme I

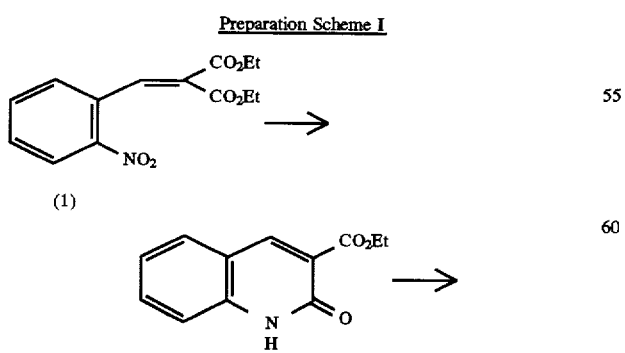

-continued
Preparation Scheme I

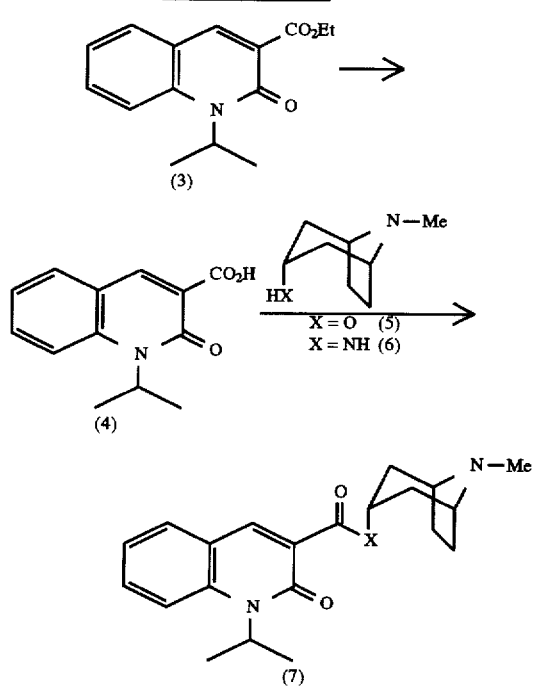

Preparation Scheme II

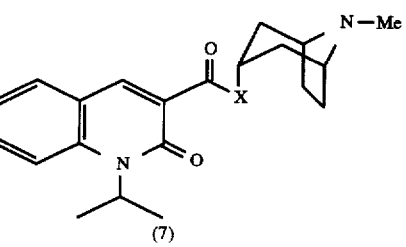

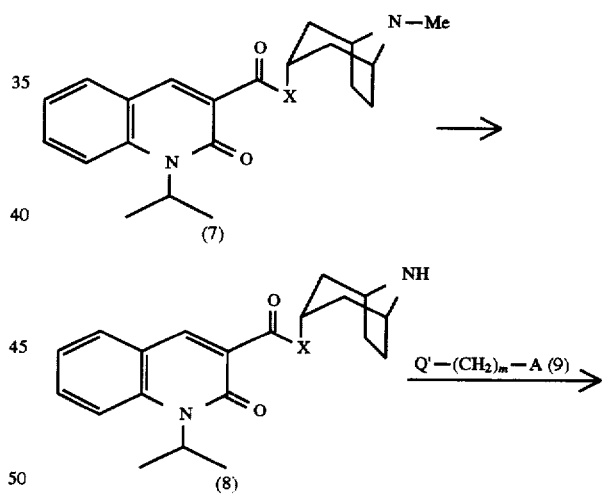

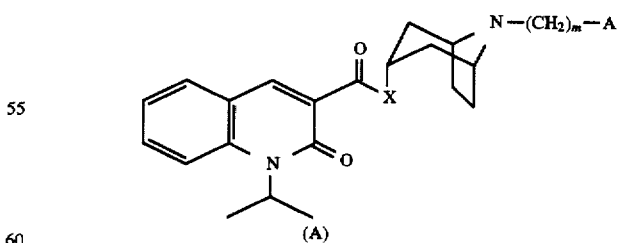

In Preparation Schemes I and II, symbols X, A and m in the formulae have the same significance as defined above and Q' in Compound (9) represents a leaving group such as a halogen atom (e.g., chlorine, bromine and iodine), tosylate or mesylate.

In Preparation Scheme I, the starting Compound (1) may be prepared according to the method described in J. Chem. Soc., 3462, 1960.

For the reductive ring closure from Compound (1) to Compound (2), reaction conditions for conventional reduction of a nitro group may be employed. The reduction and ring closure take place simultaneously to obtain Compound (2). Examples of such reaction conditions for the reduction include:

(1) catalytic reduction in an appropriate solvent using a palladium-type catalyst such as palladium-carbon, palladium black, palladium-barium sulfate and palladium-calcium carbonate, or a platinum-type catalyst such as platinum-carbon, platinum black, platinum oxide, etc., or a nickel-type catalyst such as Raney nickel; and (2) reduction in an appropriate inert solvent using iron or tin, or using sodium sulfide-ammonium chloride.

The reduction in (1) above proceeds in a solvent and examples of the solvent are water; acetic acid; an alcohol; a hydrocarbon such as hexane; an ether such as diethyl ether and tetrahydrofuran; a non-protonic polar solvent such as N,N-dimethylformamide; and a solvent mixture thereof. As a solvent employed for the reduction in (2) above, examples include water, acetic acid, methanol, ethanol and dioxane, and a solvent mixture thereof.

The reaction temperature for the reduction in (1) and (2) is generally within the range from 0° C. to the boiling point of a solvent used; the reaction time is appropriately between 30 minutes and 24 hours.

Compound (2) is N-isopropylated to form Compound (3) under conditions conventional for the N-alkylation of an acid amide. More specifically, the N-isopropylation is carried out in an appropriate solvent in the presence of a reactive derivative for introducing the isopropyl group and a base. Examples of the reactive derivative for introducing the isopropyl group include an isopropyl halide such as isopropyl iodide or isopropyl bromide. As the base employed, there are, for example, a metal alkali such as sodium and potassium; an alkali hydride such as sodium hydride and potassium hydride; an alkali alkoxide such as sodium ethoxide and potassium t-butoxide; an alkali hydroxide such as sodium hydroxide and potassium hydroxide; a carbonate such as sodium carbonate and potassium carbonate; an amine such as triethylamine, diisopropylethylamine, pyridine and N,N-dimethylaniline.

Examples of the solvent used for the N-isopropylation are water; an alcohol such as methanol and ethanol; an ether such as diethyl ether, dioxane and tetrahydrofuran; a hydrocarbon such as hexane and benzene; a non-protic polar solvent such as N,N-dimethylformamide and dimethylsulfoxide; and a solvent mixture thereof. The reaction is performed generally at 0° C. up to the boiling point of a solvent used.

In general, the reaction time is appropriately set for 30 minutes to 24 hours.

Hydrolysis of Compound (3) to give Compound (4) is carried out under conventional conditions for hydrolysis, for example, acidic hydrolysis using hydrochloric acid, hydrobromic acid, hydroiodic acid, acetic acid or sulfuric acid, or alkaline hydrolysis using sodium hydroxide, potassium hydroxide, sodium carbonate or potassium carbonate. The reaction temperature is generally between 0° C. and the boiling point of a solvent used. In general, the reaction time is appropriately set in the range of 30 minutes to 24 hours.

Esterification or amidation of Compound (4) to Compound (7) is carried out by reacting Compound (4) or its reactive derivative with tropine (Compound (5)) or with endo-3-amino-8-methyl-8-azabicyclo[3.2.1]octane (Compound (6)). Compound (6) can thus be prepared, see Journal of American Chemical Society, 79, 4194 (1957).

Examples of Compound (4) or its reactive derivatives are compounds represented by formula (12):

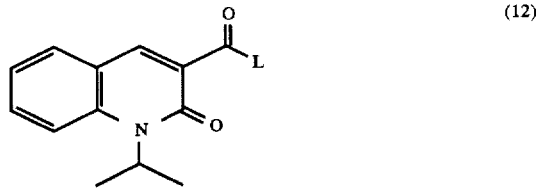

wherein L represents hydroxy group, a halogen atom, an alkoxy group, an aryloxy group, an alkoxycarbonyloxy group, an acyloxy group, imidazolyl group or azide group. Herein, the compounds of formula (12) other than those wherein L is hydroxy or ethoxy are novel compounds that are obtained in the present invention for the first time.

In formula (12), specific examples of the groups shown by L are hydroxy group; a halogen atom such as chlorine, bromine and iodine; an alkoxy group having 1 to 6 carbon atoms such as methoxy and ethoxy; a substituted or unsubstituted aryloxy group such as phenoxy, p-nitrophenoxy and pentachlorophenoxy; a $C_2$–$C_6$-alkoxycarbonyloxy group such as ethoxycarbonyloxy; a $C_2$–$C_7$-acyloxy group such as t-butylcarbonyloxy or benzoyloxy; imidazolyl group and azide group.

The reactive derivative of Compound (4) represented by formula (12) may be prepared, e.g., by the following process.

In order to prepare the reactive derivative wherein L is a halogen atom, Compound (4) is reacted with a halogenating agent such as oxalyl chloride, thionyl chloride, phosphorus trichloride, phosphorus pentachloride or phosphorus tribromide.

As the solvent for the above reaction, there may be employed dichloroethane, chloroform, benzene, toluene, tetrahydrofuran or N,N-dimethylformamide. The reaction temperature is chosen from –20° C. to the boiling point of the solvent.

In order to obtain the reactive derivative (12) wherein L is an alkoxy group, Compound (4) is reacted with an alcohol represented by formula (II):

$$R^1\text{—OH} \qquad \qquad (II)$$

wherein $R^1$ is an alkyl group.

The reaction may be carried out either in an appropriate solvent or in the absence of any solvent. Where a solvent is employed, examples of the solvent are toluene, xylene, benzene, n-hexane, tetrahydrofuran, N,N-dimethylformamide, dimethylsulfoxide, acetone, dichloromethane and chloroform. A catalyst may be used for the reaction; in this case, an acid catalyst such as hydrochloric acid, sulfuric acid or p-toluenesulfonic acid or a basic catalyst such as sodium methoxide, n-butyl lithium or sodium hydride may be employed. An appropriate temperature for the reaction is within the range of –20° C. to the boiling point of the solvent used.

Specific examples of the solvent employed are toluene, xylene, benzene, n-hexane, ether, tetrahydrofuran, dimethylsulfoxide and chloroform. An appropriate temperature for the reaction is within the range of –20° C. to the boiling point of the solvent used.

In order to obtain the reactive derivative (12) wherein L is an alkoxy group, Compound (4) is reacted with a compound represented by formula (III):

R⁴—Q¹                   (III)

wherein $R^4$ is an alkyl group and $Q^1$ represents chlorine, bromine, iodine, tosylate or mesylate, or with a sulfuric acid ester such as $R^4{}_2SO_4$.

The reaction may proceed in an appropriate solvent and specific examples of the solvent are toluene, xylene, benzene, n-hexane, tetrahydrofuran, dimethylsulfoxide, N,N-dimethylformamide, acetone and chloroform. The reaction is carried out preferably in the presence of a base. Specific examples of the base employed are sodium hydrogencarbonate, potassium hydrogencarbonate, sodium carbonate, potassium carbonate, triethylamine, diisopropylethylamine, pyridine and N,N-dimethylaniline. The temperature is appropriately within the range of −20° C. to the boiling point of the solvent employed.

The reactive derivative of formula (12) wherein L is an aryloxy group or an acyloxy group may be readily prepared in a conventional manner used for preparing an activated ester of carboxylic acid. The reactive derivative of formula (12) wherein L is an alkoxycarbonyloxy group, imidazolyl group or azide group may also be readily prepared in a conventional manner used for preparing a mixed anhydride, an activated amide or an acid azide, respectively.

Where L is an active or unstable functional group, it is preferred to use the compound (12) wherein L is hydroxy, namely, a free carboxylic acid as Compound (4).

In Preparation Scheme I, the esterification or amidation between Compound (4) or its reactive derivative and Compound (5) or Compound (6) may be carried out in a conventional manner.

For example, there may be employed a method which comprises suitably reacting the reactive derivative (12) of Compound (4) such as an acid halide a lower alkyl ester or an activated ester, or its imidazolide or mixed anhydride with Compound (5) or Compound (6); or a method which comprises directly binding Compound (4) to Compound (5) or Compound (6) using a condensing agent.

Where the acid halide is employed, the halide is reacted with Compound (5) or Compound (6) generally in a solvent inert to the reaction at a temperature of from 0° C. to the boiling point of the solvent in the presence of or absence of a base.

Examples of the solvent include ether, tetrahydrofuran, dioxane, methylene chloride, chloroform, dichloroethane, benzene, toluene, xylene, water or a mixture thereof.

Examples of the base which can be employed are sodium carbonate, potassium carbonate, sodium hydrogencarbonate, potassium hydrogencarbonate, sodium hydroxide, potassium hydroxide, pyridine, triethylamine, diisopropylethylamine, N,N-dimethylaniline, sodium hydride and n-butyl lithium.

In general, the reaction time is appropriately in the range of 30 minutes to 24 hours.

Where the reactive derivative (12) such as a lower alkyl ester or an activated ester, or its imidazolide or mixed anhydride is reacted with Compound (5) or Compound (6), known reaction conditions conventionally applied may be used.

Where the compounds are directly bound to each other using a condensing agent, Compound (4) is reacted with Compound (5) or Compound (6) generally in a solvent inert to the reaction at a temperature of from 0° C. to the boiling point of the solvent used in the presence of a condensing agent.

Examples of the solvent include ether, tetrahydrofuran, dioxane, dichloromethane, chloroform, dichloroethane, benzene, toluene, xylene, water, or a mixture thereof.

Examples of the condensing agent which can be employed are dicyclohexylcarbodiimide, carbonyldiimidazole, 2-chloro-N-methylpyridinium iodide, diphenylphosphorylazide, and diethyl cyanophosphonate.

Next, the thus obtained Compound (7) is demethylated to give Compound (8) as shown in Preparation Scheme II. The demethylation may be effected by a method using an alkyl haloformate such as chloroethyl chloroformate, or by a method using bromocyanide, iodine or N-bromosuccinimide.

Then Compound (8) is reacted with Compound (9) in a solvent such as chloroform, ethanol, toluene, N,N-dimethylformamide, tetrahydrofuran or dimethylsulfoxide at a temperature of 0° C. to the boiling point of a solvent, in the presence or absence of a base. By the reaction, the quinolinecarboxylic acid derivative of the present invention represented by formula (A) can be finally prepared.

Where a base is employed, examples of the base include triethylamine, diisopropylethylamine, N,N-dimethylaniline, pyridine, sodium carbonate, potassium carbonate, sodium hydrogencarbonate and potassium hydrogencarbonate. If necessary and desired, sodium iodide or potassium iodide etc. may be used in addition to the base above.

Compound (8) may also be prepared by the following Preparation Scheme III:

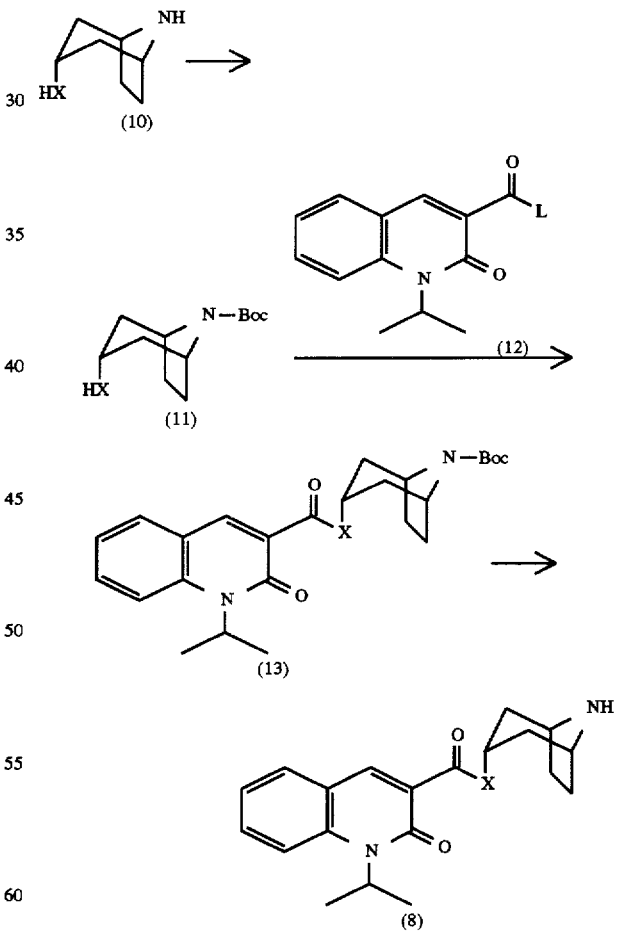

In Preparation Scheme III, symbols X and L have the same significance as defined above and Boc represents t-butoxycarbonyl group.

As shown in Preparation Scheme III, Compound (10) is reacted with, e.g., di-t-butyl dicarbonate to give Compound (11). A solvent is used for the reaction and examples of such a solvent include ether, tetrahydrofuran, dichloromethane, chloroform, toluene and benzene. The reaction temperature is appropriately chosen from the range of −20° C. to the boiling point of the solvent.

Compound (11) may be converted into Compound (13) in a manner similar to the conversion of Compound (4) into Compound (7) in Preparation Scheme I. Conversion of Compound (13) into Compound (8) is carried out by using hydrochloric acid, hydrobromic acid, sulfuric acid, acetic acid, trichloroacetic acid or trifluoroacetic acid in a solvent such as ether, tetrahydrofuran, dichloromethane, chloroform, toluene, benzene or ethyl acetate.

The reaction temperature is appropriately chosen from the range of −20° C. to the boiling point of the solvent.

The compounds of the present invention may also be prepared according to Preparation Scheme IV below.

benzoquinone; lead tetraacetate or selenium dioxide. Examples of the solvent used are dioxane, tetrahydrofuran, ether, benzene, toluene, chloroform, water or a mixture thereof. The reaction temperature is appropriately chosen from the range of −20° C. to the boiling point of the solvent. In general, the reaction time is appropriately between 30 minutes and 24 hours.

Compound (15) may also be obtained in the form of acid addition salts such as the hydrochloride.

Compound (15) may be converted into Compound (16) or Compound (4) by condensing Compound (15) with malonic acid or a malonic acid ester in the presence of or absence of a condensing agent.

Examples of the condensing agent which can be used include a hydroxide, carbonate, hydrogencarbonate, alcoholate and amide of an alkali metal; an amine such as ammonia and piperidine;, acetic acid, acetic anhydride and zinc chlo-

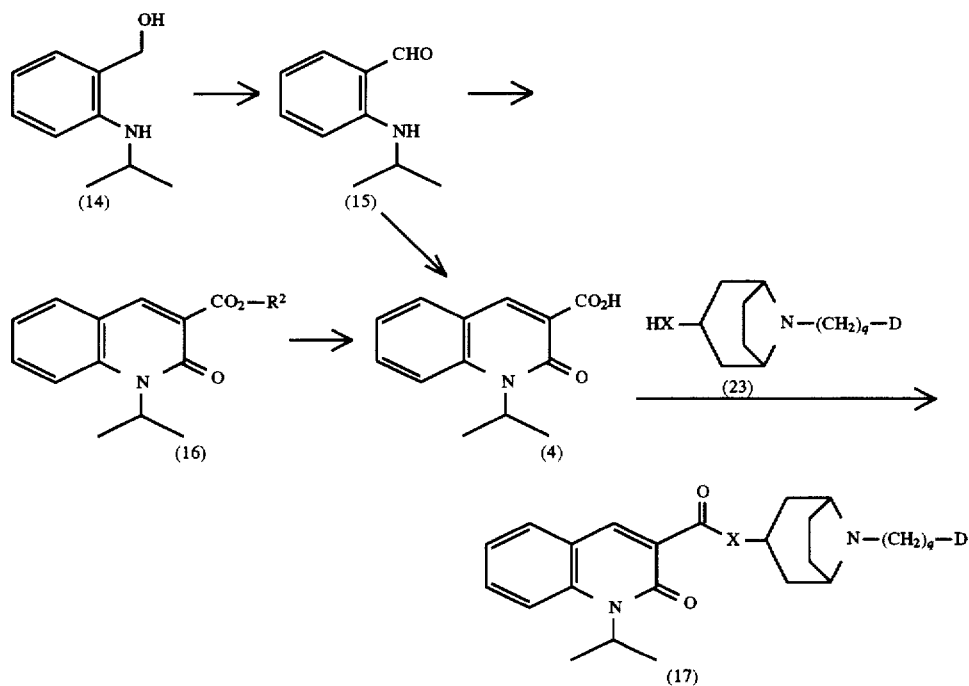

Preparation Scheme IV

In Preparation Scheme IV, symbol X in formulae (23) and (17) has the same significance as defined above; q represents an integer of 2 to 6; and D represents hydroxymethyl group, an alkoxy group having 2 to 6 carbon atoms or morpholinyl group. Specific examples of these functional groups shown by D are the same as those given for group A in formula (A). $R^2$ in Compound (16) represents an alkyl group.

As shown in Preparation Scheme IV, Compound (17) of the present invention may also be prepared using as the starting compound 2-isopropylaminobenzyl alcohol (14), which is prepared by the method described in Chem. Pharm. Bull., 34, 140 (1986).

Compound (15) can be prepared by oxidizing Compound (14) with an oxidizing agent under known conditions for oxidization. The oxidation may be carried out in a solvent, using as an oxidizing agent a transition metal compound such as manganese dioxide, activated manganese dioxide or chromic acid; an organic compound such as dimethylsulfoxide, chloranil, 2,3-dichloro-5,6-dicyano-1,4- ride. The condensing agents may be used alone or in admixture. Compound (16) or Compound (4) may also be prepared by reacting with the condensing agent in a solvent such as benzene, toluene or xylene or in the absence of a solvent. The reaction temperature is appropriately chosen from the range of −20° C. to the boiling point of the solvent. In general, the reaction time is appropriately between 30 minutes and 24 hours.

Compound (17) of the present invention may be prepared by reacting Compound (4) or its reactive derivative with Compound (23) in the manner described above, for example, by the reaction between Compound (4) and Compound (5) or (6) in Preparation Scheme I, or by the reaction between Compound (11) and Compound (12) in Preparation Scheme III.

Compound (23) in Preparation Scheme IV may be prepared according to Preparation Scheme V shown below.

Preparation Scheme V

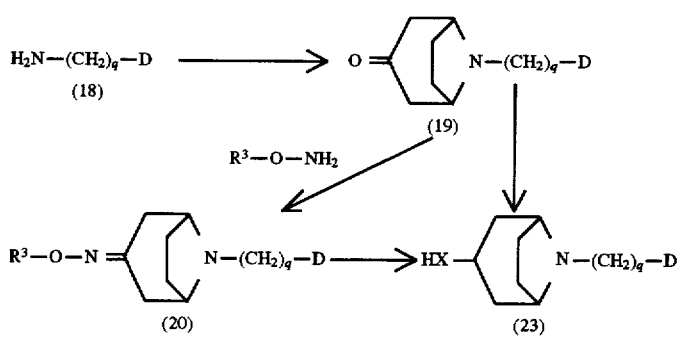

In Preparation Scheme V, symbols q, D and X have the same significance as defined above; and $R^3$ represents hydrogen, an alkyl group such as methyl, or an alkanoyl group such as acetyl.

Compound (19) in Preparation Scheme V may be prepared by reacting Compound (18) with butanedial and 1,3-acetonedicarboxylic acid or its ester, by a modification of the method disclosed in Journal of Organic Chemistry, 22, 1385 (1957).

That is, butanedial obtained by treating 2,5-dimethoxytetrahydrofuran with hydrochloric acid is reacted with Compound (18) and 1,3-acetonedicarboxylic acid in a solvent to give Compound (19). Examples of the solvent used for the reaction are a hydrated solvent of ethanol, methanol, N,N-dimethylformamide or dimethylsulfoxide; and water. The reaction temperature is appropriately chosen from the range of –20° C. to the boiling point of the solvent. In general, the reaction time is appropriately between 30 minutes and 48 hours. It is preferred to adjust the reaction solution to an acidic region. Preferably the reaction is carried out by adjusting the pH to approximately 1.5 to 4.5, using, e.g., hydrochloric acid, sodium hydrogenphosphate or sodium hydroxide.

Compound (20) is prepared by reacting Compound (19) with a hydroxylamine derivative represented by formula: $R^3$—O—$NH_2$, in a conventional manner. When Compound (20) is reduced in a conventional manner, for example, reduction with sodium in an alcohol such as isoamyl alcohol; reduction with a hydride such as sodium borohydride, lithium aluminum hydride or borane; reduction in the presence of a palladium-type catalyst such as palladium-carbon, palladium black, palladium-barium sulfate and palladium-calcium carbonate, or in the presence of a platinum-type catalyst such as platinum-carbon, platinum black, platinum oxide, etc., or in the presence of a nickel-type catalyst such as Raney nickel; whereby Compound (23) wherein X is imino is obtained.

Compound (23) wherein X is an oxygen atom may be prepared by directly reducing Compound (19) in a manner similar to the reduction described above.

From the standpoint that Compound (23) is an intermediate for preparing preferred quinolinecarboxylic acid derivatives of the present invention, Compound (23) is preferably represented by formula (24):

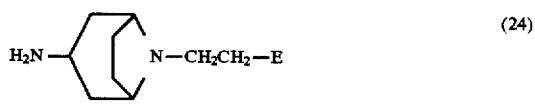

wherein E represents hydroxymethyl, morpholino or ethoxy.

Compound (17) of the present invention may also be prepared by the following Preparation Scheme VI.

Preparation Scheme VI

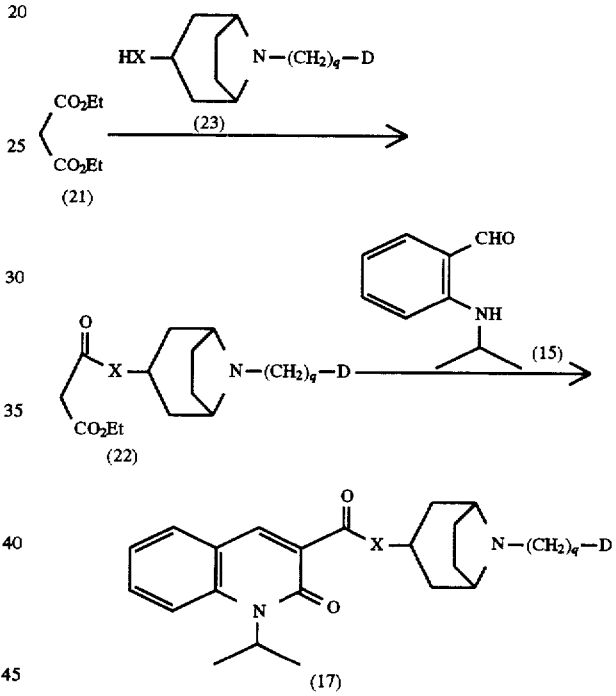

In Preparation Scheme VI, symbols X, q and D have the same significance as defined above.

Compound (22) may be prepared by condensing Compound (23) with malonic acid (21) or an ester thereof in a conventional manner, as shown in Preparation Scheme VI.

Examples of the solvent used for the condensation include hexane, benzene, toluene, xylene, tetrahydrofuran, dioxane, N,N-dimethylformamide and dimethylsulfoxide. The condensation may also be carried out in the absence of any solvent. The condensation may proceed with or without a condensing agent. Where the condensing agent is employed, an acidic condensing agent such as hydrochloric acid, sulfuric acid, p-toluenesulfonic acid, phosphoric acid, or a basic condensing agent such as sodium methoxide, n-butyl lithium or sodium hydride may be employed.

An appropriate temperature for the reaction is within the range of –20° C. to the boiling point of the solvent used. In general, the reaction time is appropriately between 30 minutes and 24 hours.

Compound (17) may be prepared by condensing Compound (22) with Compound (15) in the presence or absence of a condensing agent. Examples of the condensing agent used include a hydroxide, carbonate, hydrogencarbonate, alcoholate and amide of an alkali metal; an amine such as ammonia and piperidine;, acetic acid, acetic anhydride and zinc chloride. The condensing agents may be used alone or in admixture. Where it is preferred to use a solvent, benzene, toluene or xylene may be used; alternatively, the condensation may proceed in the absence of any solvent. The reaction temperature is appropriately chosen from the range of −20° C. to the boiling point of the solvent. In general, the reaction time is appropriately between 30 minutes and 24 hours.

The thus obtained quinolinecarboxylic acid derivative or its pharmaceutically acceptable salt of the present invention acts on serotonin 4 receptor to exhibit a receptor-stimulating activity like serotonin. That is, the compounds of the present invention accelerate the gastrointestinal motor function and improve the gastrointestinal conditions such as heartburn, anorexia, bowel pain, abdominal distension, etc., accompanied by chronic gastritis, diabetes mellitus or postoperative gastroparesis, and are thus effective for the treatment of gastro-esophagal reflux, intestinal pseudo-obstruction and constipation.

A dose of the compound of the present invention varies depending upon condition. In general, a daily dose for adult is in the range of 0.1 to 500 mg/human for oral administration and 0.01 to 100 mg/human for intravenous administration. The dose may be given at once or by dividing the daily dose into several times.

The pharmaceutical composition of the present invention comprising the compound of the present invention as an effective ingredient may be prepared into a solid preparation such as a tablet, a pill, a capsule or granules, or into an injection, liquid, an emulsion or a suppository, and provided for use.

These pharmaceutical preparations may be provided by a known method for preparing conventional pharmaceutical compositions. If necessary and desired, an additive which is conventionally used may be added to the preparations; examples of such an additive are an aid, a stabilizer, an emulsifier and a diluent.

Hereinafter the present invention will be described more specifically, by referring to Examples, Reference Examples and Experiments. The numbering of the compounds shown in the following Examples corresponds to that of the compounds used in Experiments.

EXAMPLE 1

Preparation of endo-N-(8-(2-propenyl)-8-azabicyclo [3.2.1]oct-3-yl)-1-isopropyl-2-oxo-1,2-dihydro-3-quinolinecarboxamide (Compound 1)

Following the procedures shown in Preparation Scheme II, the title compound of formula (A) wherein X is imino, m is 1 and A is vinyl was prepared.

(1) Endo-N-(8-azabicyclo[3.2.1]oct-3-yl)-1-isopropyl-2-oxo-1,2-dihydro-3-quinolinecarboxamide hydrochloride A solution of 22.4 g of endo-N-(8-methyl-8-azabicyclo [3.2.1]oct-3-yl)-1-isopropyl-2-oxo-1,2-dihydro-3-quinolinecarboxamide and 6.85 ml of 1-chloroethyl chloroformate in 100 ml of 1,2-dichloroethane was heated to reflux for an hour. After the solvent was distilled off under vacuum, 100 ml of methanol was added to the residue. The mixture was heated and stirred for an hour and then the solvent was distilled off. The residue was recrystallized from isopropanol-ethyl acetate to give 24.3 g of endo-N-(8-azabicyclo[3.2.1]oct-3-yl)-1-isopropyl-2-oxo-1,2-dihydro-3-quinolinecarboxamide hydrochloride.

mp: >270° C.

(2) Endo-N-(8-(2-propenyl)-8-azabicyclo[3.2.1]oct-3-yl)-1-isopropyl-2-oxo-1,2-dihydro-3-quinolinecarboxamide A solution of 1.11 g of endo-N-(8-azabicyclo[3.2.1]oct-3-yl)-1-isopropyl-2-oxo-1,2-dihydro-3-quinolinecarboxamide hydrochloride, 0.25 ml of 3-bromopropene and 1.2 g of potassium carbonate in 30 ml of ethanol was stirred at room temperature overnight. The reaction mixture was poured into water and extracted with chloroform. The chloroform layer was washed with water and dried over sodium sulfate. The solvent was distilled off and the residue was purified by silica gel column chromatography (chloroform:methanol=20:1). Recrystallization from ethyl acetate gave 0.53 g of endo-N-(8-(2-propenyl)-8-azabicyclo[3.2.1]oct-3-yl)-1-isopropyl-2-oxo-1,2-dihydro-3-quinolinecarboxamide.

mp: 126°–128° C. (ethyl acetate)

EXAMPLE 2

The following compounds were prepared in a manner similar to Example 1.

1) Endo-N-(8-(2-propynyl)-8-azabicyclo[3.2.1]oct-3-yl)-1-isopropyl-2-oxo-1,2-dihydro-3-quinolinecarboxamide (Compound 2)

mp: 201°–203° C. (ethyl acetate)

2) Endo-N-(8-(2-hydroxyethyl)-8-azabicyclo[3.2.1]oct-3-yl)-1-isopropyl-2-oxo-1,2-dihydro-3-quinolinecarboxamide (Compound 4)

mp: 160°–162° C. (ethyl acetate)

3) Endo-N-(8-(3-hydroxypropyl)-8-azabicyclo[3.2.1]oct-3-yl)-1-isopropyl-2-oxo-1,2-dihydro-3-quinolinecarboxamide (Compound 5)

mp: 171°–172° C. (ethyl acetate)

4) Endo-N-(8-(4-hydroxybutyl)-8-azabicyclo[3.2.1]oct-3-yl)-1-isopropyl-2-oxo-1,2-dihydro-3-quinolinecarboxamide (Compound 6)

mp: 162°–164° C. (ethyl acetate)

5) Endo-N-(8-(5-hydroxypentyl)-8-azabicyclo[3.2.1]oct-3-yl)-1-isopropyl-2-oxo-1,2-dihydro-3-quinolinecarboxamide (Compound 7)

NMR (ppm, $CDCl_3$); 1.68 (6H, d, J=7.2 Hz), 1.40–1.80 (7H, m), 1.85 (1H, s), 1.92 (1H, s), 2.10–2.30 (4H, m), 2.40–2.70 (4H, m), 3.40–3.60 (2H, m), 3.67 (2H, t, J=6.4 Hz), 4.35 (1H, q, J=7.0 Hz), 5.50–5.80 (1H, brs), 7.22–7.35 (1H, m), 7.59–7.70 (2H, m), 7.75 (1H, d, J=7.8 Hz), 8.83 (1H, s), 10.55 (1H, d, J=7.2 Hz).

6) Endo-N-(8-(6-hydroxyhexyl)-8-azabicyclo[3.2.1]oct-3-yl)-1-isopropyl-2-oxo-1,2-dihydro-3-quinolinecarboxamide hydrochloride (Compound 8)

mp: 251°–253° C. (isopropanol)

7) Endo-N-(8-(5-acetoxypentyl)-8-azabicyclo[3.2.1]oct-3-yl)-1-isopropyl-2-oxo-1,2-dihydro-3-quinolinecarboxamide hydrochloride (Compound 9)

NMR (ppm, $CDCl_3$); 1.35–1.55 (2H, m), 1.61–1.80 (6H, d, J=7.0Hz), 1.68 (6H, d, J=7.2 Hz), 2.05 (3H, s), 1.90–2.60 (8H, m), 2.70–2.95 (2H, m), 3.02–3.35 (2H, m), 3.80–3.98 (2H, m), 4.07 (2H, t, J=6.4 Hz), 4.46 (1H, q, J=6.2 Hz), 5.40–5.80 (1H, brs), 7.26–7.38 (1H, m), 7.65 (1H, s), 7.67 (1H, s), 7.77 (1H, d, J=7.8 Hz), 8.84 (1H, s), 10.65 (1H, d, J=6.4 Hz), 12.05–12.35 (1H, brs).

8) Endo-N-(8-(2-ethoxyethyl)-8-azabicyclo[3.2.1]oct-3-yl)-1-isopropyl-2-oxo-1,2-dihydro-3-quinolinecarboxamide (Compound 11)

mp: 99°–100° C. (isopropyl ether)

9) Endo-N-(8-(2-(2-methoxyethoxy)ethyl)-8-azabicyclo [3.2.1]oct-3-yl)-1-isopropyl-2-oxo-1,2-dihydro-3-quinolinecarboxamide hydrochloride (Compound 14)

10) Endo-N-(8-(2-(methylthio)ethyl)-8-azabicyclo[3.2.1]oct-3-yl)-1-isopropyl-2-oxo-1,2-dihydro-3-quinolinecarboxamide (Compound 17)

mp: 168°–169° C. (ethyl acetate-isopropyl ether)

11) Endo-N-(8-(2-(methylsulfinyl)ethyl)-8-azabicyclo[3.2.1]oct-3-yl)-1-isopropyl-2-oxo-1,2-dihydro-3-quinolinecarboxamide (Compound 18)

mp: 177°–179° C. (ethyl acetate)

12) Endo-N-(8-(2-(phenylsulfonyl)ethyl)-8-azabicyclo[3.2.1]oct-3-yl)-1-isopropyl-2-oxo-1,2-dihydro-3-quinolinecarboxamide (Compound 19)

mp: 210°–211° C. (ethyl acetate)

13) Endo-N-(8-(2-(morpholinoethyl)-8-azabicyclo[3.2.1]oct-3-yl)-1-isopropyl-2-oxo-1,2-dihydro-3-quinolinecarboxamide (Compound 20)

mp: 177°–178° C. (ethyl acetate-isopropyl ether)

14) Endo-N-(8-(2-piperidinoethyl)-8-azabicyclo[3.2.1]oct-3-yl)-1-isopropyl-2-oxo-1,2-dihydro-3-quinolinecarboxamide (Compound 21)

mp: 159°–160° C. (ethyl acetate)

15) Endo-N-(8-(tetrahydropyran-2-methyl)-8-azabicyclo[3.2.1]oct-3-yl)-1-isopropyl-2-oxo-1,2-dihydro-3-quinolinecarboxamide (Compound 22)

mp: 163°–164° C. (ethyl acetate)

16) Endo-N-(8-(2-phenoxyethyl)-8-azabicyclo[3.2.1]oct-3-yl)-1-isopropyl-2-oxo-1,2-dihydro-3-quinolinecarboxamide (Compound 23)

mp: 146°–147° C. (ethyl acetate-isopropyl ether)

17) Endo-N-(8-((ethoxycarbonyl)methyl)-8-azabicyclo[3.2.1]oct-3-yl)-1-isopropyl-2-oxo-1,2-dihydro-3-quinolinecarboxamide (Compound 25)

mp: 106°–108° C. (ethyl acetate-isopropyl ether)

18) Endo-N-(8-(carboxymethyl)-8-azabicyclo[3.2.1]oct-3-yl)-1-isopropyl-2-oxo-1,2-dihydro-3-quinolinecarboxamide (Compound 26)

mp: 244°–247° C. (methanol-ethyl acetate)

19) Endo-N-(8-(3-(ethoxycarbonyl)propyl)-8-azabicyclo[3.2.1]oct-3-yl)-1-isopropyl-2-oxo-1,2-dihydro-3-quinolinecarboxamide hydrochloride (Compound 27)

mp: 251°–252° C. (ethanol)

20) Endo-N-(8-(3-carboxypropyl)-8-azabicyclo[3.2.1]oct-3-yl)-1-isopropyl-2-oxo-1,2-dihydro-3-quinolinecarboxamide (Compound 28)

mp: >250° C. (ethanol-ethyl acetate)

21) Endo-N-(8-acetyl-8-azabicyclo[3.2.1]oct-3-yl)-1-isopropyl-2-oxo-1,2-dihydro-3-quinolinecarboxamide (Compound 29)

mp: 208°–210° C. (ethyl acetate)

22) Endo-N-(8-(2-oxopropyl)-8-azabicyclo[3.2.1]oct-3-yl)-1-isopropyl-2-oxo-1,2-dihydro-3-quinolinecarboxamide hydrochloride (Compound 30)

mp: 208°–211° C. (decompd.) (ethanol)

23) Endo-N-(8-(4-oxopentyl)-8-azabicyclo[3.2.1]oct-3-yl)-1-isopropyl-2-oxo-1,2-dihydro-3-quinolinecarboxamide (Compound 31)

mp: 101°–103° C. (isopropyl ether-n-hexane)

24) Endo-N-(8-cyanomethyl-8-azabicyclo[3.2.1]oct-3-yl)-1-isopropyl-2-oxo-1,2-dihydro-3-quinolinecarboxamide (Compound 32)

mp: 178°–181° C. (ethyl acetate-isopropyl ether)

25) Endo-N-(8-(2-cyanoethyl)-8-azabicyclo[3.2.1]oct-3-yl)-1-isopropyl-2-oxo-1,2-dihydro-3-quinolinecarboxamide (Compound 33)

mp: 177°–178° C. (ethyl acetate-isopropyl ether)

26) Endo-N-(8-carbamoylmethyl-8-azabicyclo[3.2.1]oct-3-yl)-1-isopropyl-2-oxo-1,2-dihydro-3-quinolinecarboxamide (Compound 34)

mp: >250° C. (ethanol)

EXAMPLE 3

Preparation of endo-8-(2-propenyl)-8-azabicyclo[3.2.1]oct-3-yl 1-isopropyl-2-oxo-1,2-dihydro-3-quinolinecarboxylate hydrochloride (Compound 35)

Following the procedures shown in Preparation Scheme II, the title compound of formula (A) wherein X is an oxygen atom, m is 1 and A is vinyl was prepared.

(1) Endo-(8-azabicyclo[3.2.1]oct-3-yl) 1-isopropyl-2-oxo-1,2-dihydro-3-quinolinecarboxylate A solution of 2.0 g of endo-(8-methyl-8-azabicyclo[3.2.1]oct-3-yl) 1-isopropyl-2-oxo-1,2-dihydro-3-quinolinecarboxylate and 0.61 g of 1-chloroethyl chloroformate in 50 ml of 1,2-dichloroethane was heated to reflux for an hour.

After the solvent was distilled off under vacuum, 30 ml of methanol was added to the residue. The mixture was heated and stirred for 30 minutes and the solvent was distilled off. The residue was purified by silica gel column chromatography (chloroform:NH3-saturated methanol=40:1). Recrystallization from isopropyl ether gave 1.60 g of endo-(8-azabicyclo[3.2.1]oct-3-yl) 1-isopropyl-2-oxo-1,2-dihydro-3-quinolinecarboxylate.

mp: 137°–140° C.

(2) Endo-8-(2-propenyl)-8-azabicyclo[3.2.1]oct-3-yl 1-isopropyl-2-oxo-1,2-dihydro-3-quinolinecarboxylate hydrochloride A solution of 170 mg of endo-(8-azabicyclo[3.2.1]oct-3-yl) 1-isopropyl-2-oxo-1,2-dihydro-3-quinolinecarboxylate, 60 mg of allyl bromide and 42 mg of potassium carbonate in 2 ml of N,N-dimethylformamide was stirred at room temperature overnight.

Water was added to the reaction mixture. After extracting with ethyl acetate, the organic layer was washed with saturated sodium chloride aqueous solution and dried over anhydrous sodium sulfate. The solvent was distilled off and the residue was purified by alumina column chromatography (chloroform).

The purified residue was dissolved in ethyl acetate and a 4N hydrochloric acid-ethyl acetate solution was added to the solution. The solvent was distilled off to give 130 mg of endo-8-(2-propenyl)-8-azabicyclo[3.2.1]oct-3-yl 1-isopropyl-2-oxo-1,2-dihydro-3-quinolinecarboxylate hydrochloride.

NMR (ppm, CDCl$_3$); 1.65 (6H, d, J=8.0 Hz), 2.14 (1H, s), 2.27(1H, s), 2.70–3.05 (3H, m), 3.05–3.25 (2H, m), 3.53 (2H, t, J=6.4 Hz), 3.87 (2H, s), 5.35–5.60 (3H, m), 6.30–6.55 (1H, m), 7.20–7.35 (1H, m), 7.55–7.80 (3H, m), 8.31 (1H, s), 12.20–12.50 (1H, brs).

EXAMPLE 4

The following compounds were prepared in a manner similar to Example 3.

1) Endo-8-(2-propynyl)-8-azabicyclo[3.2.1]oct-3-yl 1-isopropyl-2-oxo-1,2-dihydro-3-quinolinecarboxamide hydrochloride (Compound 36)

NMR (ppm, CDCl$_3$); 1.68 (6H, d, J=7.2 Hz), 2.25–2.35 (1H, m), 2.00–2.50 (4H, m), 2.75–2.95 (2H, m), 3.10–3.30 (2H, m), 3.70–3.95 (2H, m), 3.95–4.20 (2H, m), 5.30–5.65 (2H, m), 7.20–7.30 (1H, m), 7.55–7.71 (3H, m), 8.82 (1H, s), 12.70–12.95 (1H, brs).

2) Endo-8-(2-hydroxyethyl)-8-azabicyclo[3.2.1]oct-3-yl 1-isopropyl-2-oxo-1,2-dihydro-3-quinolinecarboxylate hydrochloride (Compound 37)

mp: 191°–193° C. (ethanol-toluene)

3) Endo-8-(3-hydroxypropyl)-8-azabicyclo[3.2.1]oct-3-yl 1-isopropyl-2-oxo-1,2-dihydro-3-quinolinecarboxylate (Compound 38)

mp: 129.5°–130.5° C. (ethyl acetate-isopropyl ether)

4) Endo-8-(4-hydroxybutyl)-8-azabicyclo[3.2.1]oct-3-yl 1-isopropyl-2-oxo-1,2-dihydro-3-quinolinecarboxylate hydrochloride (Compound 39)

mp: 209°–212.5° C. (ethanol-toluene)

5) Endo-8-(5-hydroxypentyl)-8-azabicyclo[3.2.1]oct-3-yl 1-isopropyl-2-oxo-1,2-dihydro-3-quinolinecarboxylate hydrochloride (Compound 40)

mp: 243°–245° C. (ethanol-toluene)

6) Endo-8-(6-hydroxyhexyl)-8-azabicyclo[3.2.1]oct-3-yl 1-isopropyl-2-oxo-1,2-dihydro-3-quinolinecarboxylate hydrochloride (Compound 41)

mp: 205°–207° C. (ethanol-isopropyl ether-toluene)

7) Endo-8-(2-methoxyethyl)-8-azabicyclo[3.2.1]oct-3-yl 1-isopropyl-2-oxo-1,2-dihydro-3-quinolinecarboxylate hydrochloride (Compound 42)

NMR (ppm, CDCl$_3$); 1.65 (6H, d, J=7.0 Hz), 2.08–2.30 (4H, m), 2.70–2.82 (2H, m), 3.08–3.30 (4H, m), 3.37 (3H, s), 3.90–4.12 (4H, m), 5.30–5.60 (1H, brs), 5.41 (1H, t, J=4.4 Hz), 7.20–7.30 (1H, m), 7.55–7.70 (3H, m), 8.30 (1H, s), 12.10–12.30 (1H, brs).

8) Endo-8-(2-ethoxyethyl)-8-azabicyclo[3.2.1]oct-3-yl 1-isopropyl-2-oxo-1,2-dihydro-3-quinolinecarboxylate hydrochloride (Compound 43)

mp: 185.5°–187° C. (ethanol-isopropyl ether-toluene)

9) Endo-8-(2-(2-methoxyethoxy)ethyl)-8-azabicyclo[3.2.1]oct-3-yl 1-isopropyl-2-oxo-1,2-dihydro-3-quinolinecarboxylate hydrochloride (Compound 59)

NMR (ppm, CDCl$_3$); 1.65 (6H, d, J=7.0 Hz), 2.11–2.20 (4H, m), 2.72–2.76 (2H, m), 3.16–3.26 (4H, m), 3.38 (3H, s), 3.52–3.56 (2H, m), 3.65–3.70 (2H, m), 4.06–4.16 (4H, m), 5.40–5.42 (2H, m), 7.21–7.29 (1H, m), 7.60–7.67 (3H, m), 8.31 (1H, s), 12.13 (1H, brs).

10) Endo-8-(2-diethylaminoethyl)-8-azabicyclo[3.2.1]oct-3-yl 1-isopropyl-2-oxo-1,2-dihydro-3-quinolinecarboxylate dihydrochloride (Compound 44)

mp: 240.5°–242.5° C. (chloroform-ethyl acetate)

11) Endo-8-(2-(methylthio)ethyl)-8-azabicyclo[3.2.1]oct-3-yl 1-isopropyl-2-oxo-1,2-dihydro-3-quinolinecarboxylate (Compound 45)

mp: 130°–140° C. (ethyl acetate-isopropyl ether)

12) Endo-8-(2-(phenylsulfonyl)ethyl)-8-azabicyclo[3.2.1]oct-3-yl 1-isopropyl-2-oxo-1,2-dihydro-3-quinolinecarboxylate (Compound 46)

mp: 131°–133° C. (ethyl acetate-isopropyl ether)

13) Endo-8-(2-morpholinoethyl)-8-azabicyclo[3.2.1]oct-3-yl 1-isopropyl-2-oxo-1,2-dihydro-3-quinoline-carboxylate dihydrochloride (Compound 47)

mp: >270° C. (ethanol-chloroform)

14) Endo-8-(tetrahydropyran-2-methyl)-8-azabicyclo[3.2.1]oct-3-yl 1-isopropyl-2-oxo-1,2-dihydro-3-quinolinecarboxylate hydrochloride (Compound 48)

mp: 255°–256.5° C. (ethanol-toluene-isopropyl ether)

15) Endo-8-(2-phenoxyethyl)-8-azabicyclo[3.2.1]oct-3-yl 1-isopropyl-2-oxo-1,2-dihydro-3-quinolinecarboxylate hydrochloride (Compound 49)

mp: 214.5°–217° C. (ethanol-toluene-isopropyl ether)

16) Endo-8-((ethoxycarbonyl)methyl)-8-azabicyclo[3.2.1]oct-3-yl 1-isopropyl-2-oxo-1,2-dihydro-3-quinolinecarboxylate hydrochloride (Compound 50)

mp: 191°–193.5° C. (ethanol-toluene-isopropyl ether)

17) Endo-8-(3-(ethoxycarbonyl)propyl)-8-azabicyclo[3.2.1]oct-3-yl 1-isopropyl-2-oxo-1,2-dihydro-3-quinolinecarboxylate hydrochloride (Compound 51)

NMR (ppm, CDCl$_3$); 1.26 (3H, t, J=7.0 Hz), 1.65 (6H, d, J=7.0 Hz), 2.00–2.40 (6H, m), 2.40–2.60 (2H, m), 2.85–3.10 (2H, m), 3.10–3.30 (2H, m), 3.80–4.00 (2H, m), 4.14 (2H, q, J=7.0 Hz), 5.30–5.65 (2H, m), 7.12–7.31 (1H, m), 7.50–7.70 (3H, m), 8.31 (1H, s), 11.80–12.10 (1H, brs).

18) Endo-8-(2-oxopropyl)-8-azabicyclo[3.2.1]oct-3-yl 1-isopropyl-2-oxo-1,2-dihydro-3-quinolinecarboxylate hydrochloride (Compound 52)

mp: 217°–225° C. (ethanol-toluene)

19) Endo-8-(4-oxopentyl)-8-azabicyclo[3.2.1]oct-3-yl 1-isopropyl-2-oxo-1,2-dihydro-3-quinolinecarboxylate hydrochloride (Compound 53)

mp: 230°–236° C. (ethanol-toluene-isopropyl ether)

20) Endo-8-(cyanomethyl)-8-azabicyclo[3.2.1]oct-3-yl 1-isopropyl-2-oxo-1,2-dihydro-3-quinolinecarboxylate hydrochloride (Compound 54)

mp: 209°–213° C. (ethanol-toluene)

21) Endo-8-(2-cyanoethyl)-8-azabicyclo[3.2.1]oct-3-yl 1-isopropyl-2-oxo-1,2-dihydro-3-quinolinecarboxylate (Compound 55)

mp: 132°–134° C. (ethyl acetate)

22) Endo-8-carbamoylmethyl-8-azabicyclo[3.2.1]oct-3-yl 1-isopropyl-2-oxo-1,2-dihydro-3-quinolinecarboxylate (Compound 56)

mp: 261.5°–264.5° C. (ethanol)

EXAMPLE 5

Preparation of endo-N-(8-(1,1-dimethylethoxy)carbonyl)-8-azabicyclo[3.2.1]oct-3-yl)-1-isopropyl-2-oxo-1,2-dihydro-3-quinolinecarboxamide (Compound 24)

Following the procedures shown in Preparation Scheme III, the title compound wherein X is imino in Compound (13) was prepared.

(1) 8-Benzyl-8-azabicyclo[3.2.1]octan-3-one oxime

To a solution of 65 ml of 2,5-dimethoxytetrahydrofuran in 200 ml of water was added 22 ml of conc. hydrochloric acid. The solution was stirred at room temperature for 20 minutes.

Under chilling with water, 500 ml of water, 82 ml of benzyl amine, a solution of 75 ml of conc. hydrochloric acid in 500 ml of water, 80 g of 1,3-acetonedicarboxylic acid, 44 g of Na$_2$HPO$_4$ and 200 ml of water containing 7.3 g of sodium hydroxide were successively added to the reaction mixture. The resulting mixture was stirred overnight at room temperature. After 33 ml of conc. hydrochloric acid was added to the reaction mixture, the system was stirred for further 3 hours. After washing with chloroform, 200 ml of water containing 75 g of sodium hydroxide was added to the mixture. The mixture was then extracted with chloroform.

After drying, the solvent was distilled off to give 152 g of crude 8-benzyl-8-azabicyclo[3.2.1]octan-3-one.

The crude product was dissolved in 200 ml of ethanol and 33 ml of 50% hydroxylamine aqueous solution was then added to the solution. The mixture was heated at 70° C. for 2 hours while stirring. The solvent was distilled off. Toluene was then added to the residue. Under reflux with heating, water was azeotropically removed. After the solvent was distilled off, the residue was recrystallized from ethanol to give 69.7 g of 8-benzyl-8-azabicyclo[3.2.1]octan-3-one oxime.

MS (m/z); 230 (M$^+$), 213, 158, 91.

NMR (ppm, CDCl$_3$); 1.45–1.75 (2H, m), 1.90–2.15 (2H, m), 2.14 (1H, d, J=16 Hz), 2.25 (1H, dd, J=16, 3 Hz), 2.63 (1H, dd, J=16, 3 Hz), 2.99 (1H, d, J=16 Hz), 3.30–3.43 (2H, m), 3.65 (2H, s), 7.18–7.48 (5H, m), 8.30–9.00 (1H, brs).

(2) 3-Amino-8-azabicyclo[3.2.1]octane

To a solution of 20.4 g of 8-benzyl-8-azabicyclo[3.2.1] octan-3-one oxime in 100 ml of acetic acid was added 2.0 g of platinum oxide to perform catalytic hydrogenation under a hydrogen pressure of 5 kg/cm2 at 30°–35° C. for 10 hours.

After completion of the hydrogenation, insoluble matters were filtered off and 40 ml of conc. hydrochloric acid was added to the filtrate. The solvent was distilled off under vacuum and the residue was recrystallized from ethanol to give 8.3 g of 3-amino-8-azabicyclo[3.2.1]octane hydrochloride. After 8.3 g of the hydrochloride was added to 100 ml of ethanol, a solution of 5.2 g of potassium hydroxide in 50 ml of ethanol was added to the mixture followed by stirring at room temperature for 3 hours. Insoluble matters were filtered off and the solvent was then distilled off to give 2.3 g of 3-amino-8-azabicyclo[3.2.1]octane.

MS (m/z); 126 (M$^+$), 110, 82, 68.

NMR (ppm, CDCl$_3$); 1.18–2.20 (11H, m), 3.28 (1H, t, J=7 Hz), 3.43–3.60 (2H, m).

(3) 3-Amino-8-((1,1-dimethylethoxy)carbonyl)-8-azabicyclo[3.2.1]octane

To a solution of 1.5 g of 3-amino-8-azabicyclo[3.2.1]octane in 50 ml of methylene chloride was dropwise added a solution of 2.7 ml of di-t-butyl dicarbonate in 5 ml of methylene chloride. The mixture was stirred at room temperature for 4 hours. The solvent was distilled off and the residue was subjected to silica gel column chromatography (chloroform:NH3-saturated methanol=40:1) to give 1.23 g of 3-amino-8-((1,1-dimethylethoxy)carbonyl)-8-azabicyclo[3.2.1]octane.

NMR (ppm, CDCl$_3$); 1.46 (9H, s), 1.30–2.32 (10H, m), 3.31 (1H, t, J=7 Hz), 4.00–4.39 (2H, brs).

(4) Endo-N-(8-((1,1-dimethylethoxy)carbonyl)-8-azabicyclo[3.2.1]oct-3-yl)-1-isopropyl-2-oxo-1,2-dihydro-3-quinolinecarboxamide To a solution of 1.25 g of 1-isopropyl-2-oxo-1,2-dihydro-3-quinolinecarboxylic acid in 30 ml of toluene was added 5 ml of thionyl chloride. The mixture was heated to reflux for 5 hours.

After the solvent was distilled off, 20 ml of toluene was added to the residue. By performing distillation again, an excess of thionyl chloride was removed. While vigorously agitating a mixture of 30 ml of water containing 1.5 g of sodium hydroxide and a solution of 1.2 g of 3-amino-8-((1,1-dimethylethoxy)-carbonyl)-8-azabicyclo[3.2.1]octane in 30 ml of methylene chloride, a solution of the acid chloride obtained above in 10 ml of methylene chloride was dropwise added to the mixture under ice cooling. Stirring was continued for further an hour.

After completion of the reaction, the reaction mixture was extracted with methylene chloride. The organic layer was washed and then dried. The solvent was distilled off and the residue was recrystallized from isopropyl ether to give 1.4 g of endo-N-8-((1,1-dimethylethoxy)carbonyl)-8-azabicyclo[3.2.1]oct-3-yl)-1-isopropyl-2-oxo-1,2-dihydro-3-quinolinecarboxamide.

mp: 144°–146° C.

EXAMPLE 6

Preparation of endo-N-(8-(2-methoxyethyl)-8-azabicyclo[3.2.1]oct-3-yl)-1-isopropyl-2-oxo-1,2-dihydro-3-quinolinecarboxamide hydrochloride (Compound 10)

Following the procedures shown in Preparation Scheme V, endo-3-amino-8-(2-methoxyethyl)-8-azabicyclo[3.2.1] octane which corresponds to Compound (23) wherein X is imino, q is 2 and D is methoxy was prepared. Then, the resulting octane was reacted with Compound (4) in accordance with Preparation Scheme IV to give the title compound.

(1) Endo-8-(2-methoxyethyl)-8-azabicyclo[3.2.1]octan-3-one

To a solution of 65 ml of 2,5-dimethoxytetrahydrofuran in 200 ml of water was added 22 ml of conc. hydrochloric acid. The mixture was stirred at room temperature for 20 minutes. Under chilling with water, 500 ml of water, 65 ml of 2-methoxyethylamine, 770 ml of 10% hydrochloric acid aqueous solution, 80 g of 1,3-acetonedicarboxylic acid, 44.5 g of Na$_2$HPO$_4$ and 200 ml of water containing 7.5 g of sodium hydroxide were successively added to the reaction mixture. The resulting mixture was stirred overnight at room temperature. After 33 ml of conc. hydrochloric acid was added to the reaction mixture, the system was stirred for further 6 hours.

After the reaction solution was washed with chloroform, 200 ml of water containing 75 g of sodium hydroxide was added to the reaction solution. The mixture was then extracted with chloroform. After drying, the solvent was distilled off and the residue was subjected to silica gel column chromatography (ethyl acetate:methanol=10:1). Distillation under vacuum gave 7.2 g of endo-8-(2-methoxyethyl)-8-azabicyclo[3.2.1]octan-3-one.

bp: 139° C. (14 mmHg) IR ν (cm$^{-1}$, neat); 3401, 2953, 1713, 1349, 1122.

MS (m/z); 183 (M$^+$), 138, 126, 96.

NMR (ppm, CDCl$_3$); 1.61 (2H, dd, J=14.5, 7.7 Hz), 1.98–2.12 (2H, m), 2.19 (2H, d, J=16.7 Hz), 2.73 (2H, dd, J=17.6, 3.8 Hz), 2.83 (2H, t, J=5.6 Hz), 3.39 (3H, s), 3.56–3.75 (4H, m).

(2) Endo-8-(2-methoxyethyl)-8-azabicyclo[3.2.1]octan-3-one oxime

After 2.9 g of 50% hydroxylamine aqueous solution was added to a solution of 4 g of -8-(2-methoxyethyl)-8-azabicyclo[3.2.1]octan-3-one in 40 ml of ethanol, the mixture was stirred at room temperature for 2 hours.

The solvent was distilled off and the residue was purified by silica gel column chromatography (chloroform:methanol=20:1) to give 4.5 g of -8-(2-methoxyethyl)-8-azabicyclo[3.2.1]octan-3-one oxime.

NMR (ppm, CDCl$_3$); 1.38–1.73 (2H, m), 1.85–2.32 (4H, m), 2.53–2.67 (2H, m), 2.72 (2H, t, J=5.9 Hz), 2.89–3.05 (1H, m), 3.37 (3H, s), 3.39–3.51 (2H, m), 3.57 (2H, t, J=5.9 Hz), 9.26 (1H, brs).

(3) Endo-3-amino-8-(2-methoxyethyl)-8-azabicyclo[3.2.1] octane dihydrochloride

To a solution of 4.5 g of endo-8-(2-methoxyethyl)-8-azabicyclo[3.2.1]octan-3-one oxime in 40 ml of acetic acid was added 500 mg of platinum oxide to perform catalytic hydrogenation under a hydrogen pressure of 5 kg/cm$^2$ at 30°–35° C. for 10 hours.

After completion of the hydrogenation, insoluble matters were filtered off and 6 ml of conc. hydrochloric acid was added to the filtrate. The solvent was distilled off. The residue was then dried and recrystallized from ethanol to give 3.4 g of endo-3-amino-8-(2-methoxyethyl)-8-azabicyclo[3.2.1]octane dihydrochloride.

mp: 266° C. (decompd.)

(4) Endo-N-(8-(2-methoxyethyl)-8-azabicyclo[3.2.1]oct-3-yl)-1-isopropyl-2-oxo-1,2-dihydro-3-quinolinecarboxamide hydrochloride A solution of 700 mg of 1-isopropyl-2-oxo-1,2-dihydro-3-quinolinecarboxylic acid and 1.1 ml of thionyl chloride in 15 ml of toluene was stirred for an hour with heating. After the solvent was distilled off, toluene was added to the residue. After toluene was again distilled off, the residue was dissolved in 10 ml of tetrahydrofuran.

Under ice cooling, the solution was dropwise added to 20 ml of 50% tetrahydrofuran aqueous solution containing 940 mg of 3-amino-8-(2-methoxyethyl)-8-azabicyclo[3.2.1] octane dihydrochloride and 650 mg of sodium hydroxide. The mixture was stirred at room temperature for 3 hours.

After completion of the reaction, the reaction mixture was diluted with water. The dilution was extracted with ethyl acetate. The organic layer was successively washed with water and saturated sodium chloride aqueous solution, followed by drying over anhydrous sodium sulfate. The solvent was distilled off and the residue was subjected to silica gel column chromatography (chloroform:methanol=9:1) to give endo-N-(8-(2-methoxyethyl)-8-azabicyclo[3.2.1]oct-3-yl)-1-isopropyl-2-oxo-1,2-dihydro-3-quinolinecarboxamide.

The product was further dissolved in ethyl acetate and then, 4N hydrochloric acid-ethyl acetate solution was added to the solution to give 760 mg of endo-N-(8-(2-methoxyethyl)-8-azabicyclo[3.2.1]oct-3-yl)-1-isopropyl-2-oxo-1,2-dihydro-3-quinolinecarboxamide hydrochloride.

m.p.; 247°–249° C.

NMR (ppm. CDCl$_3$); 1.68 (6H, d, J=7.0 Hz), 2.10 (1H, s), 2.18 (1H, s), 2.25–2.60 (4H, m), 3.10–3.20 (2H, m), 3.20–3.30 (1H, m), 3.38 (3H, s), 3.30–3.55 (1H, m), 3.95–4.18 (4H, m), 4.07 (1H, q, J=4.0 Hz), 5.30–5.80 (1H, brs), 7.26–7.36 (1H, m), 7.65 (1H, s), 7.67 (1H, s), 7.77 (1H, d, J=7.6 Hz), 8.85 (1H, s), 10.68 (1H, d, J=6.6 Hz), 11.90–12.25 (1H, brs).

EXAMPLE 7

The following compounds were prepared in a manner similar to Example 6.

1) Endo-N-(8-(2,2,2-trifluoroethyl)-8-azabicyclo[3.2.1]oct-3-yl)-1-isopropyl-2-oxo-1,2-dihydro-3-quinolinecarboxamide hydrochloride (Compound 3)

mp: 241.0°–244.0° C. (ethanol)

2) Endo-N-(8-(2-diethylaminoethyl)-8-azabicyclo[3.2.1]oct-3-yl)-1-isopropyl-2-oxo-1,2-dihydro-3-quinolinecarboxamide dihydrochloride (Compound 16)

mp: 179.0°–186.0° C. (ethanol-ethyl acetate-acetone)

Reference Example 1

Preparation of endo-8-(4-methoxyphenyl)-8-azabicyclo[3.2.1]oct-3-yl 1-isopropyl-2-oxo-1,2-dihydro-3-quinolinecarboxylate (Compound 57)

For a reference example, the title compound corresponding to a compound of formula (A) wherein X is an oxygen atom, m is 0 and A is 4-methoxyphenyl was prepared.

(1) 8-(4-Methoxyphenyl)-8-azabicyclo[3.2.1]octan-3-one

To a solution of 36 ml of 2,5-dimethoxytetrahydrofuran in 100 ml of water was added 12 ml of conc. hydrochloric acid. The mixture was stirred at room temperature for 20 minutes. Under chilling with water, 200 ml of water, 50 g of 4-methoxyaniline, 43 ml of conc. hydrochloric acid, 43.5 g of 1,3-acetonedicarboxylic acid, 19.2 g of Na$_2$HPO$_4$ and 3.9 g of sodium hydroxide were successively added to the reaction mixture. The resulting mixture was stirred overnight at room temperature. After 18 ml of conc. hydrochloric acid was added to the reaction mixture, stirring was continued for further 6 hours.

After the reaction solution was washed with chloroform, 30 ml of water containing 39 g of sodium hydroxide was added to the reaction solution. The mixture was then extracted with chloroform. After drying, the solvent was distilled off and the residue was subjected to silica gel column chromatography (chloroform:NH$_3$-saturated methanol=100:1). Recrystallization from ethanol gave 6.75 g of 8-(4-methoxyphenyl)-8-azabicyclo[3.2.1]octan-3-one.

mp: 133°–134° C.

(2) Endo-8-(4-methoxyphenyl)-8-azabicyclo[3.2.1]octan-3-ol

A solution of 4 g of 8-(4-methoxyphenyl)-8-azabicyclo[3.2.1]octan-3-one in 80 ml of tetrahydrofuran was cooled to −70° C. and 51 ml of diisobutyl aluminum hydride (1M tetrahydrofuran solution) was then dropwise added to the solution.

After completion of the reaction, 12 ml of 50% tetrahydrofuran aqueous solution was added to the reaction mixture and insoluble matters were filtered off. The solvent was distilled off and dried. Recrystallization from ethyl acetate-n-hexane gave 1.5 g of endo-8-(4-methoxyphenyl)-8-azabicyclo[3.2.1]octan-3-ol.

NMR (ppm, CDCl$_3$); 1.42–1.49 (1H, m), 1.50–1.57 (1H, m), 1.57–1.66 (1H, m), 2.00–2.11 (2H, m), 2.22–2.43 (4H, m), 3.75 (3H, s), 3.96–4.06 (1H, m), 4.06–4.14 (2H, m), 6.71–6.91 (4H, m).

(3) Endo-8-(4-methoxyphenyl)-8-azabicyclo[3.2.1]oct-3-yl 1-isopropyl-2-oxo-1,2-dihydro-3-quinolinecarboxylate To a solution of 1.2 g of 1-isopropyl-2-oxo-1,2-dihydro-3-quinolinecarboxylic acid in 10 ml of toluene was added 1.5 ml of thionyl chloride. The mixture was stirred at 80° C. for an hour. After the solvent was distilled off under vacuum, 10 ml of tetrahydrofuran was added to the residue. The solvent was again distilled off under vacuum.

To the residue was added 10 ml of tetrahydrofuran to give a tetrahydrofuran solution of the acid chloride.

Under ice cooling, 2.7 ml of n-butyl lithium (1.56M n-hexane solution) was dropwise added to 10 ml of tetrahydrofuran containing 1 g of endo-8-(4-methoxyphenyl)-8-azabicyclo[3.2.1]octan-3-ol. The mixture was stirred for 30 minutes. To the solution was dropwise added the tetrahydrofuran solution of the acid chloride previously prepared. Stirring was continued overnight at room temperature.

After the solvent was distilled off, water was added to the residue, followed by extraction with chloroform. The chloroform layer was dried over anhydrous sodium sulfate. After the solvent was distilled off, the residue was purified by silica gel column chromatography (chloroform) to give 220 mg of endo-8-(4-methoxyphenyl)-8-azabicyclo[3.2.1]oct-3-yl) 1-isopropyl-2-oxo-1,2-dihydro-3-quinolinecarboxylate.

mp: 136.5°–139° C. (ethyl acetate-isopropyl ether)

Reference Example 2

As a reference example, endo-8-(2-thiazolyl)-8-azabicyclo[3.2.1]oct-3-yl 1-isopropyl-2-oxo-1,2-dihydro-3-quinolinecarboxylate hydrochloride (Compound 58) corresponding to the compound of formula (A) wherein X is an oxygen atom, m is 0 and A is 2-thiazolyl was prepared in a manner similar to Reference Example 1.

mp: 218.5°–221.5° C. (chloroform-isopropyl ether)

EXAMPLE 8

Preparation of 1-isopropyl-2-oxo-1,2-dihydro-3-quinolinecarbonyl chloride

The title compound corresponding to the compound of formula (12), wherein L is chlorine and which is an intermediate for preparing the quinolinecarboxylic acid derivative of the present invention, was prepared.

A solution of 3.88 g of 1-isopropyl-2-oxo-1,2-dihydro-3-quinolinecarboxylic acid and 5.0 ml of thionyl chloride in 50 ml of toluene was stirred at 100° C. for 5 hours. After toluene was distilled off under vacuum, toluene was again added to the residue. The solvent was again distilled off under vacuum to give 4.22 g of 1-isopropyl-2-oxo-1,2-dihydro-3-quinolinecarbonyl chloride.

mp: 114°–116° C.

EXAMPLE 9

Preparation of 4-nitrophenyl 1-isopropyl-2-oxo-1,2-dihydro-3-quinolinecarboxylate The title compound corresponding to the compound of formula (12), wherein L is 4-nitrophenyloxy and which is an intermediate for preparing the quinolinecarboxylic acid derivative, was prepared.

To a solution of 1.0 g of 1-isopropyl-2-oxo-1,2-dihydro-3-quinolinecarbonyl chloride in 30 ml of toluene was added 0.55 g of p-nitrophenol. The mixture was stirred overnight at room temperature. After solvent was distilled off, the residue was extracted with ether. The solvent was again distilled off. The resulting solid was washed with a small quantity of cold ether to give 0.56 g of 4-nitrophenyl 1-isopropyl-2-oxo-1,2-dihydro-3-quinolinecarboxylate.

mp: 80°–82° C.

EXAMPLE 10

Endo-3-amino-8-(2-morpholinoethyl)-8-azabicyclo[3.2.1]octane trihydrochloride

Following the procedures shown in Preparation Scheme V, the title compound corresponding to Compound (23) wherein X is imino, q is 2 and D is morpholino was prepared as an intermediate for producing the quinolinecarboxylic acid derivative.

(1) 8-(2-Morpholinoethyl)-8-azabicyclo[3.2.1]octan-3-one

To a solution of 16.2 ml of 2,5-dimethoxytetrahydrofuran in 50 ml of water was added 6 ml of conc. hydrochloric acid. The mixture was stirred at room temperature for 20 minutes. Thereafter, 150 ml of water, 25 ml of 1-(2-aminoethyl) morpholine, 20 ml of conc. hydrochloric acid and 20.1 g of 1,3-acetonedicarboxylic acid were successively added to the reaction mixture. Furthermore, a solution of 8.8 g of Na$_2$HPO$_4$ and 2.5 g of sodium hydroxide in 100 ml of water was added to the mixture. Thereafter the pH was adjusted to the range of 2 to 3. After stirring overnight at room temperature, the reaction solution was washed with chloroform. Potassium carbonate was added to the mixture to render alkaline, followed by extraction with chloroform. The organic layer was washed with water and then dried over anhydrous sodium sulfate. The solvent was then distilled off. The residue was purified by silica gel column chromatography (chloroform:NH$_3$-saturated methanol=20:1) to give 26.7 g of 8-(2-morpholinoethyl)-8-azabicyclo[3.2.1]octan-3-one.

NMR (ppm, CDCl$_3$); 1.50–1.77 (3H, m), 1.95–2.10 (2H, m), 2.20 (2H, d, J=15 Hz), 2.40–2.80 (9H, m), 3.50–3.61 (2H, m), 3.68–3.77 (4H, m)

(2) 8-(2-Morpholinoethyl)-8-azabicyclo[3.2.1]octan-3-one oxime

After 22.2 ml of 50% hydroxylamine aqueous solution was added to a solution of 40.0 g of 8-(2-morpholinoethyl)-8-azabicyclo[3.2.1]octan-3-one in 200 ml of ethanol, the mixture was stirred at room temperature for an hour. The solvent was distilled off and toluene was added followed by azeotropic distillation. After the solvent was distilled off, the residue was purified by silica gel column chromatography (chloroform:NH$_3$-saturated methanol=20:1) to give 32.8 g of 8-(2-morpholinoethyl)-8-azabicyclo[3.2.1]octan-3-one oxime.

MS (m/z); 253 (M$^+$)

NMR (ppm, CDCl$_3$); 1.40–1.68 (2H, m), 1.80–2.29 (4H, m), 2.40–2.73 (9H, m), 2.95 (1H, d, J=15 Hz), 3.30–3.47 (2H, m), 3.65–3.78 (4H, m), 8.98 (1H, brs).

(3) Endo-3-amino-8-(2-morpholinoethyl)-8-azabicyclo[3.2.1]octane trihydrochloride To a solution of 15.0 g of 8-(2-morpholinoethyl)-8-azabicyclo[3.2.1]octan-3-one oxime in 150 ml of acetic acid was added 1.5 g of platinum oxide to perform catalytic hydrogenation under a hydrogen pressure of 5 kg/cm$^2$ at 40° C. for 8 hours. After completion of the hydrogenation, insoluble matters were filtered off and 20 ml of conc. hydrochloric acid was added to the filtrate. The mixture was concentrated to dryness under vacuum. Recrystallization from methanol-ethanol gave 5.9 g of endo-3-amino-8-(2-morpholinoethyl)-8-azabicyclo[3.2.1]octane trihydrochloride.

mp: >213° C. (decompd.)

NMR (ppm, CDCl$_3$) (free); 1.00–1.50 (4H, m), 1.88–2.20 (6H, m), 2.40–2.55 (8H, m), 3.13–3.27 (3H, m), 3.65–3.78 (4H, m)

EXAMPLE 11

Preparation of endo-3-amino-8-(3-hydroxypropyl)-8-azabicyclo[3.2.1]octane

Following the procedures shown in Preparation Scheme V, the title compound corresponding to Compound (23) wherein X is imino, q is 2 and D is hydroxymethyl was prepared as an intermediate for producing the quinolinecarboxylic acid derivative.

1) 8-(3-Hydroxypropyl)-8-azabicyclo[3.2.1]octan-3-one

In a nitrogen flow, 45 ml of conc. hydrochloric acid was added to a solution of 120 ml of 2,5-dimethoxytetrahydrofuran in 300 ml of water while stirring at room temperature. Twenty minutes after, the reaction solution became homogenous. Thereafter, 450 ml of water, a solution of 105 ml of 3-amino-1-propanol and 138 ml of conc. hydrochloric acid in 600 ml of water, a solution of 150 g of 1,3-diacetonedicarboxylic acid in 700 ml of water and a solution of 66 g of Na$_2$HPO$_4$ in 300 ml of water were successively added to the homogenous reaction solution. Furthermore, about 215 ml of 40% sodium hydroxide aqueous solution was added to the mixture. The pH of the resulting solution was then adjusted to the range of 3 to 4. After bubbling was confirmed, the mixture was stirred overnight. Then conc. hydrochloric acid was added to adjust the pH of the reaction solution to 3. The reaction solution was heated to 80° C. and stirred until bubbling of carbon dioxide gas was not observed. After completion of the reaction, the reaction solution was cooled and sodium hydroxide aqueous solution was added thereto to render alkaline. Thereafter sodium chloride was added for salting out, followed by extraction with chloroform. The chloroform layer was washed with water and then dried over anhydrous sodium sulfate. The solvent was distilled off to give 8-(3-hydroxypropyl)-8-azabicyclo[3.2.1]octan-3-one as the crude product.

NMR (ppm, CDCl$_3$); 1.58–1.69 (2H, m), 1.71–1.86 (2H, m), 2.00–2.30 (4H, m), 2.59–2.72 (2H, m), 2.81 (2H, t, J=5.9 Hz), 3.58–3.70 (2H, m), 3.88 (2H, t, J=5.3 Hz), 5.10 (1H, brs)

(2) 8-(3-Hydroxypropyl)-8-azabicyclo[3.2.1]octan-3-one oxime hydrochloride

The crude product of 8-(3-hydroxypropyl)-8-azabicyclo[3.2.1]octan-3-one was dissolved in 1200 ml of ethanol and 72.9 g of 50% hydroxylamine aqueous solution was added to the solution at room temperature, while stirring. After completion of the reaction, the solvent was distilled off and toluene was added. The solvent was again distilled off and ethanol was added to the residue. An equimolar volume of conc. hydrochloric acid was then added to the mixture. The precipitated crystals were filtered to give 161 g of 8-(3-hydroxy-propyl)-8-azabicyclo[3.2.1]octan-3-one oxime hydrochloride.

NMR (ppm, methanol-$d_4$); 1.75–2.08 (4H, m), 2.21–2.56 (4H, m), 2.83–2.93 (1H, m), 3.19–3.45 (3H, m), 3.73 (2H, t, J=5.7 Hz), 4.14–4.20 (2H, m)

(3) Endo-3-amino-8-(3-hydroxypropyl)-8-azabicyclo[3.2.1]octane

A solution of 100 g of 8-(3-hydroxypropyl)-8-azabicyclo[3.2.1]octan-3-one oxime hydrochloride and 5 g of platinum oxide in 500 ml of acetic acid was reacted for about 18 hours under a hydrogen pressure of 5.0–5.4 kg/cm², while maintaining at 45° to 46° C. After adding water, the reaction mixture was filtered and the filtrate was concentrated. After 50 ml of water and 100 ml of methanol were added to the concentrate, a solution of 38.4 g of oxalic acid in 200 ml of methanol was added thereto and further 200 ml of methanol was added to the mixture, followed by stirring overnight at room temperature. The precipitated crystals were filtered and dried to give 71.3 g of endo-3-amino-8-(3-hydroxypropyl)-8-azabicyclo[3.2.1]octane hydrochloride oxalate.

mp: 175°–185° C. (decompd.)

In 300 ml of water was dissolved 30.0 g of endo-3-amino-8-(3-hydroxypropyl)-8-azabicyclo[3.2.1]octane hydrochloride oxalate, and 48.3 g of potassium hydrogencarbonate was then dissolved in the solution. The mixture was stirred at room temperature for 4 hours. Furthermore 300 ml of ethanol was added thereto. After stirring for an hour, precipitated insoluble matters were filtered off and the filtrate was concentrated. Again 300 ml of ethanol was added to the concentrate. The precipitated insoluble matters were filtered off and the filtrate was concentrated. The concentrate was dissolved in 300 ml of chloroform. After drying over anhydrous sodium sulfate, the solvent was distilled off to give endo-3-amino-8-(3-hydroxy-propyl)-8-azabicyclo[3.2.1]octane.

NMR (ppm, CDCl$_3$); 1.43–1.50 (2H, m), 1.54–1.71 (2H, m), 1.85–2.14 (6H, m), 2.60 (2H, t, J=5.6 Hz), 3.19–3.37 (3H, m), 3.85 (2H, t, J=5.2 Hz)

EXAMPLE 12

Preparation of endo-3-amino-8-(2-ethoxyethyl)-8-azabicyclo[3.2.1]octane

The title compound corresponding to Compound (23) wherein X is imino, q is 2 and D is ethoxy was prepared in a manner similar to Example 11, as an intermediate for producing the quinolinecarboxylic acid derivative.

1) 8-(2-Ethoxyethyl)-8-azabicyclo[3.2.1]octan-3-one

NMR (ppm, CDCl$_3$); 1.22 (3H, t, J=7.0 Hz), 1.53–1.64 (2H, m), 1.90–2.23 (4H, m), 2.65–2.75 (2H, m), 2.82 (2H, t, J=6.0 Hz), 3.45–3.71 (6H, m) 2) 8-(2-Ethoxyethyl)-8-azabicyclo[3.2.1]octan-3-one oxime MS (m/z); 212 (M$^+$), 153

NMR (ppm, CDCl$_3$); 1.21 (3H, t, J=7.0 Hz), 1.42–1.69 (2H, m), 1.86–2.28 (4H, m), 2.59 (1H, dd, J=14.9, 3.3 Hz), 2.71 (2H, t, J=6.3 Hz), 2.95 (1H, d, J=15.6 Hz), 3.42–3.63 (6H, m), 8.68 (1H, brs)

3) Endo-3-amino-8-(2-ethoxyethyl)-8-azabicyclo[3.2.1]octane

MS (m/z); 198 (M$^+$), 82

NMR (ppm, CDCl$_3$); 1.20 (3H, t, J=7.0 Hz), 1.31–1.69 (4H, m), 1.84–2.00 (4H, m), 2.00–2.23 (2H, m), 2.57 (2H, t, J=6.7 Hz), 3.19–3.25 (3H, m), 3.45–4.01 (4H, m)

EXAMPLE 13

Preparation of endo-N-(8-(3-hydroxypropyl)-8-azabicyclo[3.2.1]oct-3-yl)-1-isopropyl-2-oxo-1,2-dihydro-3-quinolinecarboxamide (Compound 5)

Following the procedures shown in Preparation Scheme IV, the title compound corresponding to Compound (17) wherein X is imino, q is 2 and D is hydroxymethyl was prepared.

1) 2-Isopropylaminobenzyl alcohol

While maintaining at 0° to 5° C., a solution of 140 g of sodium borohydride in 500 ml of 0.5% sodium hydroxide aqueous solution was dropwise added over 2 hours to a solution mixture of 150 g of 2-aminobenzyl alcohol, 300 g of sodium acetate trihydrate, 850 ml of acetic acid, 950 ml of water, 275 ml of ethanol and 500 ml of acetone. Stirring was continued at the same temperature for an hour. Thereafter the reaction mixture was neutralized with potassium carbonate, followed by extraction with hexane. The organic layer was washed with water and then with saturated sodium chloride aqueous solution. The solvent was distilled off under vacuum. Distillation under vacuum gave 142 g of 2-isopropylaminobenzyl alcohol.

bp: 110°–114° C. (4 mmHg)

2) 2-Isopropylaminobenzaldehyde

While heating a solution of 40 g of 2-isopropylaminobenzyl alcohol in 200 ml toluene at 100° C., 58 g in total of activated manganese dioxide was added several times to the solution. After stirring at the same temperature for 30 minutes, insoluble matters were filtered off. The solvent was distilled off to give 2-isopropylaminobenzaldehyde.

NMR (ppm, CDCl$_3$); 1.27 (6H, d, J=6.4 Hz), 3.67–3.83 (1H, m), 6.59–6.73 (2H, m), 7.31–7.43 (1H, m), 7.44 (1H, dd, J=7.6, 1.4 Hz), 8.26 (1H, s), 9.79 (1H, s)

The thus obtained 2-isopropylaminobenzaldehyde was dissolved in toluene and 4N hydrochloric acid ethyl acetate solution was added thereto under ice cooling. Thus, 42.6 g of 2-isopropylaminobenzaldehyde hydrochloride was obtained.

3-1) Ethyl 1-isopropyl-2-oxo-1,2-dihydro-3-quinolinecarboxylate

A solution of 133.7 g of 2-isopropylaminobenzaldehyde hydrochloride, 200 g of diethyl malonate, 70 ml of piperidine, 70 ml of acetic acid, 50 g of potassium carbonate and 1.5 liter of toluene was heated to reflux for 10 hours. The reaction solution was washed with water and then with saturated sodium hydrogencarbonate aqueous solution, and dried over anhydrous magnesium sulfate. The solvent was distilled off to give 256 g of ethyl 1-isopropyl-2-oxo-1,2-dihydro-3-quinolinecarboxylate as the crude product.

3-2) Ethyl 1-isopropyl-2-oxo-1,2-dihydro-3-quinolinecarboxylate

A solution of 20.0 g of 2-isopropylaminobenzaldehyde, 29.4 g of diethyl malonate, 10 ml of piperidine, 10 ml of acetic acid and 500 ml of toluene was heated to reflux for 13 hours. The reaction solution was washed with water and then with saturated sodium hydrogencarbonate aqueous solution, and dried over anhydrous magnesium sulfate. The solvent was distilled off to give 52 g of ethyl 1-isopropyl-2-oxo-1,2-dihydro-3-quinolinecarboxylate as the crude product.

4-1) 1-Isopropyl-2-oxo-1,2-dihydro-3-quinolinecarboxylic acid

While stirring a solution of 256 g of the crude ethyl 1-isopropyl-2-oxo-1,2-dihydro-3-quinolinecarboxylate in 200 ml of ethanol under ice cooling, 500 ml of an aqueous solution of 52 g of sodium hydroxide was added to the solution. The mixture was stirred at room temperature for 2 hours.

The reaction solution was washed with toluene and conc. hydrochloric acid was then added to render the system acidic. The precipitates were filtered, washed with water and dried to give 126.7 g of 1-isopropyl-2-oxo-1,2-dihydro-3-quinolinecarboxylic acid.

4-2) 1-Isopropyl-2-oxo-1,2-dihydro-3-quinolinecarboxylic acid

A solution of 5.0 g of 2-isopropylaminobenzaldehyde, 4.8 g of malonic acid, 5 ml of piperidine, 5 ml of acetic acid and 50 ml of toluene was heated to reflux for 3.5 hours. The reaction solution was washed with water. The crude product partly precipitated was filtered. The filtrate was extracted with 2N sodium hydroxide aqueous solution and the precipitates above was dissolved in the extract. The resulting solution was washed with toluene and aqueous hydrochloric acid solution was then added thereto to render the system acidic. The precipitates were washed with water and dried to give 3.9 g of 1-isopropyl-2-oxo-1,2-dihydro-3-quinolinecarboxylic acid.

5) 1-Isopropyl-2-oxo-1,2-dihydro-3-quinolinecarbonyl chloride

A solution of 3.88 g of 1-isopropyl-2-oxo-1,2-dihydro-3-quinolinecarboxylic acid and 5.0 ml of thionyl chloride in 50 ml of toluene was stirred at 100° C. for 5 hours. After toluene was distilled off under vacuum, toluene was again added to the residue. The solvent was again distilled off under vacuum to give 4.22 g of 1-isopropyl-2-oxo-1,2-dihydro-3-quinolinecarbonyl chloride.

mp: 114°–116° C.

6-1) Endo-N-(8-(3-hydroxypropyl)-8-azabicyclo[3.2.1]oct-3-yl)-1-isopropyl-2-oxo-1,2-dihydro-3-quinolinecarboxamide In 150 ml of toluene was dissolved 18.7 g of endo-3-amino-8-(3-hydroxypropyl)-8-azabicyclo[3.2.1]octane. While stirring at room temperature, a solution of 24.1 g of 1-isopropyl-2-oxo-1,2-dihydro-3-quinolinecarbonyl chloride in 200 ml of toluene was dropwise added to the above solution. Stirring was continued for an hour. The reaction solution was concentrated. Thereafter 150 ml of methanol and 50 ml of 20% sodium hydroxide aqueous solution were added to the concentrate. The mixture was stirred at room temperature for 30 minutes. The solvent was distilled off and water was added to the residue, followed by extraction with chloroform.

The chloroform layer was washed with water and dried over anhydrous sodium sulfate. The solvent was distilled off and the residue was recrystallized from ethanol-ethyl acetate to give 22.9 g of endo-N-(8-(3-hydroxypropyl)-8-azabicyclo (3.2.1]oct-3-yl)-1-isopropyl-2-oxo-1,2-dihydro-3-quinolinecarboxamide.

6-2) Endo-N-(8-(3-hydroxypropyl)-8-azabicyclo[3.2.1]oct-3-yl)-1-isopropyl-2-oxo-1,2-dihydro-3-quinolinecarboxamide In 50 ml of toluene was suspended 5.0 g of 1-isopropyl-2-oxo-1,2-dihydro-3-quinolinecarboxylic acid. After 7.7 ml of thionyl chloride was added to the suspension, the mixture was heated at 80° C. for an hour with stirring. After completion of the reaction, the solvent was distilled off. Again 50 ml of toluene was added to dissolve the residue. The solvent was distilled off to give the acid chloride.

In 40 ml of water was dissolved 6.71 g of endo-N-(8-(3-hydroxypropyl)-8-azabicyclo[3.2.1]octane hydrochloride oxalate. After a solution of 4.85 g of potassium hydroxide in 40 ml of water was added to the solution above, the mixture was stirred at room temperature for 20 minutes. After 70 ml of tetrahydrofuran was added thereto, a solution obtained by dissolving the acid chloride previously obtained in 50 ml of toluene was dropwise added to the mixture. Stirring was continued for 30 minutes. The reaction solution was concentrated. Thereafter 150 ml of methanol and 50 ml of 20% potassium hydroxide aqueous solution were added to the concentrate. The resulting mixture was stirred at room temperature for 30 minutes. The reaction solution was concentrated and water was added to the concentrate. The mixture was then extracted with chloroform. After washing with water, the extract was dried over anhydrous sodium sulfate. The solvent was distilled off and the residue was recrystallized from ethanol-ethyl acetate to give 6.5 g of endo-N-(8-(3-hydroxypropyl)-8-azabicyclo[3.2.1]oct-3-yl)-1-isopropyl-2-oxo-1,2-dihydro-3-quinolinecarboxamide.

mp: 167°–169° C. (ethanol-isopropyl ether)

MS (m/z); 397 (M$^+$), 128

NMR (ppm, CDCl$_3$); 1.68 (6H, d, J=8 Hz), 1.62–1.78 (2H, m), 1.80–1.96 (2H, m), 2.00–2.38 (6H, m), 2.72 (2H, t, J=6 Hz), 3.42 (2H, brs), 3.88 (2H, t, J=6 Hz), 4.30 (1H, q, J=7 Hz), 5.45–5.80 (1H, brs), 7.23–7.33 (1H, m), 7.56–7.70 (2H, m), 7.75 (1H, d, J=7 Hz), 8.83 (1H, s), 10.51 (1H, d, J=8 Hz)

EXAMPLE 14

Preparation of endo-N-(8-(2-morpholinoethyl)-8-azabicyclo[3.2.1]oct-3-yl)-1-isopropyl-2-oxo-1,2-dihydro-3-quinolinecarboxamide (Compound 20)

Following the procedures shown in Preparation Scheme IV, the title compound corresponding to Compound (17) wherein X is imino, q is 2 and D is morpholino was prepared.

In 50 ml of toluene was suspended 1.03 g of 1-isopropyl-2-oxo-1,2-dihydro-3-quinolinecarboxylic acid. After 5.0 ml of thionyl chloride was added to the suspension, the mixture was heated at 100° C. for 3 hours with stirring. After completion of the reaction, the solvent was distilled off. Again 20 ml of toluene was added to dissolve the residue. The solvent was distilled off to give the acid chloride.

A solution of 3.2 g of endo-3-amino-8-(2-morpholinoethyl)-8-azabicyclo[3.2.1]octane in 50 ml of tetrahydrofuran was dropwise added to the acid chloride under ice cooling. The mixture was stirred at room temperature for an hour. The reaction solution was diluted with ethyl acetate and then washed successively with saturated sodium hydrogencarbonate and with saturated sodium chloride aqueous solution. After drying over anhydrous sodium sulfate, the solvent was distilled off and the residue was recrystallized from ethyl acetate to give 1.7 g of endo-N-(8-(2-morpholinoethyl)-8-azabicyclo[3.2.1]oct-3-yl)-1-isopropyl-2-oxo-1,2-dihydro-3-quinolinecarboxamide.

mp: 178°–180° C. (ethanol-ethyl acetate)

NMR (ppm, CDCl$_3$); 1.67–1.80 (8H, m), 2.05–2.31 (6H, m), 2.49–2.58 (8H, m), 3.27 (2H, brs), 3.70–3.74 (4H, m), 4.28 (1H, q, J=7.3 Hz), 5.60 (1H, brs), 7.25–7.32 (1H, m), 7.61–7.64 (2H, m), 7.75 (1H, d, J=7.7 Hz), 8.83 (1H, s), 10.48 (1H, d, J=7.8 Hz)

Reference Example 3

Endo-N-(8-azabicyclo[3.2.1]oct-3-yl)-1-isopropyl-2-oxo-1,2-dihydro-3-quinolinecarboxamide The title compound corresponding to Compound (8), wherein X is imino and which is an intermediate for preparing the quinolinecarboxylic acid derivative, was prepared according to Preparation Scheme III.

Several drops of trifluoroacetic acid was added to a solution of 1.0 g of endo-N-(8-((1,1-dimethylethoxy)carbonyl)- 8-azabicyclo[3.2.1]oct-3-yl)-1-isopropyl-2-oxo-1,2-dihydro-3-quinolinecarboxamide in 10 ml of methylene chloride. After stirring at room temperature for 30 minutes, the reaction mixture was washed with saturated sodium bicarbonate aqueous solution and dried over anhydrous sodium sulfate.

The solvent was distilled off and the residue was recrystallized from ethyl acetate to give 0.58 g of endo-N-(8-azabicyclo[3.2.1]oct-3-yl)-1-isopropyl-2-oxo-1,2-dihydro-3-quinolinecarboxamide.

mp: 205°–207° C. (ethyl acetate)

MS (m/z); 339 (M$^+$), 214

NMR (ppm, CDCl$_3$); 1.70 (6H, d, J=7.0 Hz), 1.91–2.48 (8H, m), 3.81 (2H, brs), 4.40 (1H, q, J=6.9 Hz), 5.60 (1H, brs), 7.24–7.33 (1H, m), 7.61–7.68 (2H, m), 7.75 (1H, d, J=7.0 Hz), 8.84 (1H, s), 10.60 (1H, d, J=7.0 Hz)

Reference Example 4

Preparation of endo-3-amino-8-(2,2,2-trifluoroethyl)-8-azabicyclo[3.2.1]octane dihydrochloride The title compound corresponding to Compound (23), wherein X is imino, q is 1 and D is trifluoromethyl, was prepared as the intermediate according to Preparation Scheme V.

1) 8-(2,2,2-Trifluoroethyl)-8-azabicyclo[3.2.1]octan-3-one

MS (m/z); 207, 150

NMR (ppm, CDCl$_3$); 1.66 (2H, d, J=7.8 Hz), 1.95–2.15 (2H, m), 2.24 (2H, dd, J=17.2, 1.6 Hz), 2.68 (2H, dd, J=16.4, 4.6 Hz), 3.15 (2H, q, J=9.2 Hz), 3.50–3.70 (2H, m)

2) 8-(2,2,2-Trifluoroethyl)-8-azabicyclo[3.2.1]octan-3-one oxime

MS (m/z); 222, 205

NMR (ppm, CDCl$_3$); 1.50–1.80 (2H, m), 1.80–2.05 (2H, m), 2.10–2.30 (2H, m), 2.57 (1H, dd, J=15.2, 3.6 Hz), 3.00–3.10 (1H, m), 3.00 (2H, q, J=9.2 Hz), 3.35–3.50 (2H, m)

3) Endo-3-amino-8-(2,2,2-trifluoroethyl)-8-azabicyclo[3.2.1]octane dihydrochloride MS (m/z); 208 (M$^+$), 150

NMR (ppm, DMSO-d$_6$); 1.87 (1H, s), 1.95 (1H, s), 2.00–2.38 (4H, m), 2.38–2.78 (2H, m), 3.25–3.50 (1H, m), 3.50–4.30 (4H, m), 8.42 (3H, brs)

Reference Example 5

Preparation of endo-3-amino-8-(5-acetyloxypentyl)-8-azabicyclo[3.2.1]octane

The title compound corresponding to Compound (23), wherein X is imino, q is 5 and D is acetyloxy, was prepared as the intermediate according to Preparation Scheme V.

1) 8-(5-Hydroxypentyl)-8-azabicyclo[3.2.1]octan-3-one

MS (m/z); 211 (M$^+$), 154, 138

NMR (ppm, CDCl$_3$); 1.31–1.82 (8H, m), 1.83–2.12 (3H, m), 2.52–2.77 (4H, m), 2.19 (2H, dd, J=17.0, 2.0 Hz), 3.67 (2H, t, J=6.5 Hz), 3.46–3.60 (2H, m)

2) 8-(5-Hydroxypentyl)-8-azabicyclo[3.2.1]octan-3-one oxime

MS (m/z); 226 (M$^+$), 154

NMR (ppm, CDCl$_3$); 1.30–1.75 (9H, m), 1.75–2.05 (2H, m), 2.10 (1H, d, J=15.4 Hz), 2.15–2.27 (1H, m), 2.49 (2H, t, J=6.6 Hz), 2.45–2.65 (1H, m), 2.96 (1H, d, J=15.4 Hz), 3.25–3.45 (2H, m), 3.65 (2H, t, J=6.2 Hz), 7.85–8.06 (1H, brs)

3) Endo-3-amino-8-(5-acetyloxypentyl)-8-azabicyclo[3.2.1]octane dihydrochloride

NMR (ppm, DMSO-d$_6$); 1.22–1.50 (2H, m), 1.50–1.88 (4H, m), 1.99 (3H, s), 2.05–2.30 (4H, m), 2.60–2.96 (4H, m), 3.02–3.18 (1H, m), 3.25–3.61 (3H, m), 3.88–3.99 (2H, m), 4.00 (2H, t, J=7.0 Hz), 8.42 (3H, br), 10.80 (1H, brs)

Reference Example 6

Preparation of endo-3-amino-8-(2-(N,N-diethylamino)ethyl)-8-azabicyclo[3.2.1]octane trihydrochloride The title compound corresponding to Compound (23), wherein X is imino, q is 2 and D is diethylamino, was prepared as the intermediate according to Preparation Scheme V.

1) 8-(2-(N,N-Diethylamino)ethyl)-8-azabicyclo[3.2.1]octan-3-one

MS (m/z); 224 (M$^+$), 86

NMR (ppm, CDCl$_3$); 1.05 (6H, t, J=7.2 Hz), 1.59 (2H, d, J=7.8 Hz), 2.15 (1H, s), 2.45–2.85 (13H, m), 3.50–3.70 (2H, m)

2) 8-(2-(N,N-Diethylamino)ethyl)-8-azabicyclo[3.2.1]octan-3-one oxime

MS (m/z); 239 (M$^+$), 86

NMR (ppm, CDCl$_3$); 1.08 (6H, t, J=7.2 Hz), 1.45–1.70 (2H, m), 1.85–2.30 (5H, m), 2.50–2.75 (8H, m), 2.96 (1H, d, J=15.6 Hz), 3.33–3.50 (2H, m)

3) Endo-3-amino-8-(2-(N,N-diethylamino)ethyl)-8-azabicyclo[3.2.1]octane trihydrochloride MS (m/z); 225 (M$^+$), 82

NMR (ppm, DMSO-d$_6$); 1.26 (6H, t, J=7.2 Hz), 2.00–2.40 (5H, m), 2.60–2.90 (2H, m), 2.90–3.28 (4H, m), 3.28–3.80 (6H, m), 3.85–4.20 (2H, m), 8.51 (3H, brs), 11.10–11.35 (1H, brs), 11.35–11.80 (1H, brs)

Reference Example 7

Preparation of endo-8-(2,2,2-trifluoroethyl)-8-azabicyclo[3.2.1]octan-3-ol

The title compound corresponding to Compound (23), wherein X is oxygen, q is 1 and D is trifluoromethyl, was prepared as the intermediate according to Preparation Scheme V. Specifically, the title compound can be prepared according to Reference Example 1 (1) and (2).

MS (m/z): 209 (M$^+$), 192, 164, 150

Reference Example 8

Preparation of ethyl endo-N-(8-(2-ethoxyethyl)-8-azabicyclo[3.2.1]oct-3-yl)carbamoylacetate The title compound corresponding to Compound (22), wherein X is imino, q is 2 and D is ethoxy, was prepared as the intermediate according to Preparation Scheme VI.

A solution of 16.44 g of endo-3-amino-8-(2-ethoxyethyl)-8-azabicyclo[3.2.1]octane and 63 ml of diethyl malonate in 150 ml of toluene was reacted for 3 hours under reflux with heating. After completion of the reaction, the reaction mixture was extracted with 10% aqueous hydrochloric acid solution. Potassium carbonate was added to the aqueous layer to render alkaline, followed by extraction with chloroform. The chloroform layer was washed and dried over anhydrous sodium sulfate. The solvent was distilled off and the residue was purified by silica gel column chromatography (chloroform:NH3-saturated methanol=50:1) to give 20.7 g of ethyl endo-N-(8-(2-ethoxyethyl)-8-azabicyclo[3.2.1]oct-3-yl)carbamoylacetate.

NMR (ppm, CDCl₃); 1.20 (3H, t, J=7.0 Hz), 1.30 (3H, t, J=7.2 Hz), 1.55–2.27 (8H, m), 2.57 (2H, t, J=6.4 Hz), 3.19–3.29 (4H, m), 3.45–3.57 (4H, m), 4.06–4.27 (3H, m), 7.92 (1H, d, J=3.5 Hz)

Reference Example 9

Preparation of ethyl endo-N-(8-(2-morpholinoethyl) -8-azabicyclo[3.2.1]oct-3-yl)carbamoylacetate The title compound corresponding to Compound (22), wherein X is imino, q is 2 and D is morpholino, was prepared in a manner similar to Reference Example 4, as the intermediate.

MS (m/z); 353 (M⁺), 253

NMR (ppm, CDCl₃); 1.30 (3H, t, J=7.0 Hz), 1.51–1.68 (2H, m), 1.68–1.91 (3H, m), 2.00–2.24 (4H, m), 2.34–2.62 (7H, m), 3.17–3.32 (4H, m), 3.64–3.75 (4H, m), 4.12 (1H, q, J=7.5 Hz), 4.23 (2H, q, J=7.0 Hz), 7.87–8.01 (1H, br)

EXAMPLE 15

Preparation of endo-N-(8-(2-ethoxyethyl)-8-azabicyclo[3.2.1]oct-3-yl)-1-isopropyl-2-oxo-1,2-dihydro-3-quinolinecarboxamide (Compound 11)

The title compound corresponding to Compound (17), wherein X is imino, q is 2 and D is ethoxy, was prepared according to Preparation Scheme VI.

A solution of 40.97 g of ethyl endo-N-(8-(2-ethoxyethyl)-8-azabicyclo[3.2.1]oct-3-yl)carbamoylacetate, 25.96 g of 2-isopropylaminobenzaldehyde hydrochloride, 19.28 ml of piperidine, 18.60 ml of acetic acid and 21.56 g of potassium carbonate in 600 ml of toluene was heated for 5 hours with stirring. After completion of the reaction, the reaction mixture was washed with water. The organic layer was dried over anhydrous sodium sulfate. The solvent was distilled off and the residue was purified by silica gel column chromatography (chloroform:NH₃-saturated methanol=50:1) to give 28.31 g of endo-N-(8-(2-ethoxyethyl)-8-azabicyclo [3.2.1]oct-3-yl)-1-isopropyl-2-oxo-1,2-dihydro-3-quinolinecarboxamide.

Reference Example 10

The following compounds are prepared in a manner similar to Reference Example 4.

1) Ethyl endo-N-(8-(3-hydroxypropyl)-8-azabicyclo [3.2.1]oct-3-yl)carbamoylacetate 2) Ethyl endo-N-(8-(2-methoxyethyl)-8-azabicyclo[3.2.1] oct-3-yl)carbamoylacetate 3) Ethyl endo-(8-(2-morpholinoethyl)-8-azabicyclo [3.2.1]oct-3-yl)oxycarbonylacetate 4) Ethyl endo-(8-(3-hydroxypropyl)-8-azabicyclo[3.2.1] oct-3-yl)oxycarbonylacetate 5) Ethyl endo-(8-(2-methoxyethyl)-8-azabicyclo[3.2.1] oct-3-yl)oxycarbonylacetate Reference Example 11

Preparation of endo-(8-methyl-8-azabicyclo[3.2.1] oct-3-yl) 1-isopropyl-2-oxo-1,2-dihydro-3-quinolinecarboxylate The title compound corresponding to Compound (7), wherein X is oxygen, was prepared as the intermediate according to Preparation Scheme I.

1) Ethyl 2-oxo-1,2-dihydro-3-quinolinecarboxylate

In 700 ml of acetic acid was dissolved 45 g of diethyl 2-nitrobenzylidenemalonate (J. Org. Chem., 3462, 1960). While maintaining at 80° C., 53 g in total of iron powders were added several times to the solution. Stirring was continued for further 2 hours.

After the temperature was then reverted to room temperature, the reaction mixture was filtered through Celite and the filtrate was concentrated under vacuum. The resulting oily substance was purified from silica gel column chromatography (chloroform:methanol=10:1) to give 21.3 g of ethyl 2-oxo-1,2-dihydro-3-quinolinecarboxylate.

mp: 160°–163.2° C. (ethyl acetate)

2) Ethyl 1-isopropyl-2-oxo-1,2-dihydro-3-quinolinecarboxylate

After 20 g of ethyl 2-oxo-1,2-dihydro-3-quinolinecarboxylate was added to a solution of 4.45 g of sodium hydride in 100 ml of dimethylformamide, 31.5 g of isopropyl iodide was added to the mixture, followed by stirring at 70° C. for 8 hours. DMF was distilled off under vacuum. The residue was then poured onto water followed by extraction with ethyl acetate. The organic layer was washed with water and then with saturated sodium chloride aqueous solution and dried over anhydrous sodium sulfate.

The solvent was distilled off under vacuum. The resulting oily substance was purified by silica gel column chromatography (ethyl acetate:n-hexane=4:1) to give 1.55 g of ethyl 1-isopropyl-2-oxo-1,2-dihydro-3-quinolinecarboxylate.

mp: 54°–57° C. (ethyl acetate)

3) 1-Isopropyl-2-oxo-1,2-dihydro-3-quinoline-carboxylic acid

A solution of 1.55 g of ethyl 1-isopropyl-2-oxo-1,2-dihydro-3-quinolinecarboxylate and 0.28 g of sodium hydroxide in 10 ml of ethanol and 2 ml of water was stirred overnight at room temperature. The solvent was distilled off and dil. hydrochloric acid was added to the residue. The precipitated solid was filtered, washed with water and dried to give 0.24 g of 1-isopropyl-2-oxo-1,2-dihydro-3-quinolinecarboxylic acid.

mp: 168°–169° C. (ethyl acetate)

4) Endo-(8-methyl-8-azabicyclo[3.2.1]oct-3-yl) 1-isopropyl-2-oxo-1,2-dihydro-3-quinolinecarboxylate To a suspension of 1 g of 1-isopropyl-2-oxo-1,2-dihydro-3-quinolinecarboxylic acid in 10 ml of tetrahydrofuran was added 1.6 ml of thionyl chloride. The mixture was stirred at 80° C. for an hour. After the solvent was distilled off under vacuum, 10 ml of tetrahydrofuran was added to the residue. The solvent was again distilled off under vacuum and 20 ml of tetrahydrofuran was added to the residue to form a tetrahydrofuran solution of the acid chloride.

Under ice cooling, 3.5 ml of n-butyl lithium (1.56M n-hexane solution) was dropwise added to a solution of 740 mg of tropine in 10 ml of tetrahydrofuran. The mixture was stirred for 30 minutes. The tetrahydrofuran solution of the acid chloride previously prepared was dropwise added to the solution. Stirring was continued overnight at room temperature. The solvent was distilled off and 2N hydrochloric acid was added thereto. After washing with ethyl acetate, the aqueous layer was rendered basic with sodium hydrogencarbonate. Thereafter the mixture was extracted with chloroform. The chloroform layer was dried over anhydrous sodium sulfate. The solvent was distilled off and the residue was purified by silica gel column chromatography (chloroform:methanol=20:1) to give 530 mg of endo-(8-methyl-8-azabicyclo[3.2.1]oct-3-yl) 1-isopropyl-2-oxo-1,2-dihydro-3-quinolinecarboxylate.

MS (m/z); 354 (M⁺), 310, 269, 172, 124

IR ν (cm⁻¹, Neat); 2937, 1733, 1652, 1211, 1034, 754.

NMR (ppm, CDCl₃);
1.66 (6H, d, J=6.9 Hz), 1.88 (1H, s), 1.92 (1H, s), 2.00–2.30 (6H, m), 2.32 (3H, s), 3.17 (2H, s), 5.27 (1H, t, J=5.4 Hz), 5.30–5.70 (1H, brs), 7.19–7.30 (1H, m), 7.55–7.68 (3H, m), 8.22 (1H, s).

Reference Example 12

Preparation of endo-N-(8-methyl-8-azabicyclo [3.2.1]oct-3-yl)-1-isopropyl-2-oxo-1,2-dihydro-3-quinolinecarboxamide The title compound corresponding to Compound (7), wherein X is imino, was prepared as the intermediate according to Preparation Scheme I.

A solution of 0.5 g of 1-isopropyl-2-oxo-1,2-dihydro-3-quinolinecarboxylic acid in 5 ml of thionyl chloride was stirred to reflux for 2 hours. After thionyl chloride was thoroughly distilled off under vacuum, 3 ml of benzene was added to the residue. Under ice cooling a solution of 0.36 g of endo-3-amino-8-methyl-8-azabicyclo[3.2.1]octane in 3 ml of benzene was dropwise added to the benzene solution of the acid chloride described above. The mixture was stirred at room temperature for 2 hours. After ethyl acetate was added thereto, the organic layer was washed with water and then with saturated sodium bicarbonate aqueous solution and dried over anhydrous magnesium sulfate. The solvent was distilled off under vacuum. The resulting residue was purified by alumina column chromatography (chloroform) to give 390 mg of endo-N-(8-methyl-8-azabicyclo[3.2.1]oct-3-yl)-1-isopropyl-2-oxo-1,2-dihydro-3-quinolinecarboxamide.

mp: 175.8°–177.8° C. (ethyl acetate)

MS (m/z); 353 (M⁺), 214, 172, 84.

IR ν (cm⁻¹, Neat); 3263, 1673, 1528, 1206.

NMR (ppm, CDCl₃); 1.68 (6H, d, J=7.2 Hz), 1.76 (1H, s), 1.83 (1H, s), 2.00–2.40 (6H, m), 2.34 (3H, s), 3.10–3.28 (2H, m), 4.30 (1H, q, J=7.2 Hz), 5.40–5.90 (1H, m), 7.22–7.33 (1H, m), 7.55–7.70 (2H, m), 7.75 (1H, d, J=7.8 Hz), 8.83 (1H, s), 10.48 (1H, d, J=7.2 Hz).

Experiments

The numbering of the compounds used in Experiments 1 through 4 corresponds to the numbering of those shown in Examples. Table 1 shows the relationship in numbering.

TABLE 1

| Compound | X | m | A |
|---|---|---|---|
| 1 | NH | 1 | CH=CH₂ |
| 2 | NH | 1 | C≡CH |
| 3 | NH | 1 | CF₃ |
| 4 | NH | 2 | OH |
| 5 | NH | 3 | OH |
| 6 | NH | 4 | OH |
| 7 | NH | 5 | OH |
| 8 | NH | 6 | OH |
| 9 | NH | 5 | OAc |

TABLE 1-continued

| Compound | X | m | A |
|---|---|---|---|
| 10 | NH | 2 | OMe |
| 11 | NH | 2 | OEt |
| 14 | NH | 2 | O(CH₂)₂OMe |
| 16 | NH | 2 | NEt₂ |
| 17 | NH | 2 | SMe |
| 18 | NH | 2 | SOMe |
| 19 | NH | 2 | SO₂Ph |
| 20 | NH | 2 | -N(morpholino) |
| 21 | NH | 2 | -N(piperidino) |
| 22 | NH | 1 | tetrahydropyran-O- |
| 23 | NH | 2 | phenyl-O- |
| 24 | NH | 0 | CO₂-t-Bu |
| 25 | NH | 1 | CO₂Et |
| 26 | NH | 1 | CO₂H |
| 27 | NH | 3 | CO₂Et |
| 28 | NH | 3 | CO₂H |
| 29 | NH | 0 | COMe |
| 30 | NH | 1 | COMe |
| 31 | NH | 3 | COMe |
| 32 | NH | 1 | CN |
| 33 | NH | 2 | CN |
| 34 | NH | 1 | CONH₂ |
| 35 | O | 1 | CH=CH₂ |
| 36 | O | 1 | C≡CH |
| 37 | O | 2 | OH |
| 38 | O | 3 | OH |
| 39 | O | 4 | OH |
| 40 | O | 5 | OH |
| 41 | O | 6 | OH |
| 42 | O | 2 | OMe |
| 43 | O | 2 | OEt |
| 44 | O | 2 | NEt₂ |
| 45 | O | 2 | SMe |
| 46 | O | 2 | SO₂Ph |
| 47 | O | 2 | -N(morpholino) |
| 48 | O | 1 | tetrahydropyran-O- |

TABLE 1-continued

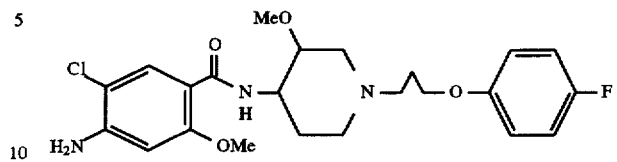

| Compound | X | m | A |
|---|---|---|---|
| 49 | O | 2 | (phenoxy) |
| 50 | O | 1 | CO₂Et |
| 51 | O | 3 | CO₂Et |
| 52 | O | 1 | COMe |
| 53 | O | 3 | COMe |
| 54 | O | 1 | CN |
| 55 | O | 2 | CN |
| 56 | O | 1 | CONH₂ |
| 57 (Comparison) | O | 0 | (4-methoxyphenyl) |
| 58 (Comparison) | O | 0 | (thiazolyl-methyl) |
| 59 | O | 2 | O(CH₂)₂OMe |

Experiment 1
Stimulating activity on serotonin 4 receptor

Stimulating activity on serotonin 4 receptor (5-HT$_4$) of the quinolinecarboxylic acid derivative of the present invention was examined by measuring twitch responses in guinea pig ileum, according to the method described in Craig, D. A. and Clarke D. E., The Journal of Pharmacology and Experimental Therapeutics, 252, 1378–1386, 1990: "Pharmacological characterization of a neuronal receptor for 5-hydroxytryptamine in guinea pig ileum with properties similar to the 5-hydroxytryptamine 4 receptor".

1) Method

From Harley guinea pigs weighing 250 to 400 g, a section of ileum 10 to 20 cm proximal to the ileocecal junction was removed. Longitudinal muscle strips obtained from the ileum were used for this assay. The preparations were suspended in Krebs' solution at 32 to 34° C., bubbled continuously with 95% O$_2$ and 5% CO$_2$, and subjected to initial tension of about 0.8 g. Responses were recorded isometrically. Twitch responses were evoked by electrical stimulation (0.2 Hz, 1 msec pulse duration). The preparations were stimulated at supramaximal voltage for 2 to 3 hours, and were then allowed to equilibrate for about 1 hour at submaximal voltage. After it was confirmed that the twitch responses were enhanced by 10$^{-8}$M serotonin, each agonist was examined on its activity for twitch responses. The preparations were left for at least 45 minutes before cumulative addition of each agonist.

The quinolinecarboxylic acid derivatives of the present invention were employed as sample compounds. For comparison, the following compounds were employed. These compounds were diluted by dissolving them in distilled water or in DMSO. Each sample compound and cisapride were prepared in such a manner that the concentration of DMSO in Bath is 0.3% or less.

Comparative Compound 1: Cisapride

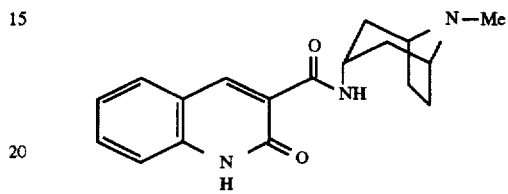

Comparative Compound 2: compound claimed in U.S. Pat. No. 5,106,851

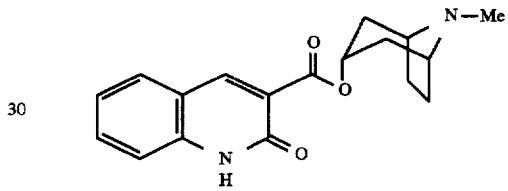

Comparative Compound 3: compound specifically disclosed in U.S. Pat. No. 5,106,851

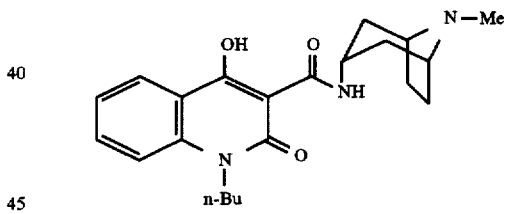

Comparative Compound 4: compound specifically disclosed in European Patent Application No. 0458636A1

2) Results

The ED$_{50}$ value of the stimulating activity on serotonin 4 receptor, which is the concentration of the activity for enhancing the twitch response by 50%, when the maximum contraction of a sample compound is made 100%, was determined. The data obtained was analyzed by RS1 (BBN Software Product Co.).

The results are shown in Table 2 below.

Table 2

Stimulating activity on 5-HT$_4$ receptor (twitch response in guinea pig ileum)

| Compound | ED$_{50}$ (nM) | Compound | ED$_{50}$ (nM) |
|---|---|---|---|
| 1 | 59.2 | 37 | 16.1 |
| 4 | 45.9 | 38 | 11.9 |
| 5 | 32.0 | 39 | 16.6 |
| 6 | 38.5 | 40 | 25.5 |
| 7 | 30.8 | 41 | 50.9 |
| 8 | 62.3 | 42 | 18.4 |

Table 2-continued

Stimulating activity on 5-HT$_4$ receptor (twitch response in guinea pig ileum)

| Compound | ED$_{50}$ (nM) | Compound | ED$_{50}$ (nM) |
|---|---|---|---|
| 9 | 33.0 | 43 | 15.2 |
| 10 | 15.0 | 44 | 72.6 |
| 11 | 18.7 | 45 | 29.5 |
| 17 | 48.0 | 46 | 46.5 |
| 19 | 86.6 | 47 | 30.8 |
| 20 | 25.5 | 48 | 55.9 |
| 22 | 24.0 | 49 | 39.0 |
| 26 | 66.1 | 51 | 23.0 |
| 27 | 19.3 | 52 | 24.6 |
| 28 | 91.4 | 53 | 26.4 |
| 30 | 11.5 | 55 | 27.3 |
| 31 | 52.3 | 56 | 31.4 |
| 33 | 35.8 | 57 (comparison) | >3000 |
| 34 | 61.9 | 58 (comparison) | 1140 |
| 35 | 54.4 | 59 | 73.7 |
|  |  | Comparative Compound 1 | 271.3 |
|  |  | Comparative Compound 2 | >3000 |
|  |  | Comparative Compound 3 | >3000 |
|  |  | Comparative Compound 4 | >3000 |

As is appreciated from the results shown in Table 2, the quinolinecarboxylic acid derivatives of the resent invention exhibited a potent stimulating activity on 5-HT$_4$ receptor.

Experiment 2.
Effect on inhibition of 5-HT$_4$ receptor-binding

The effect on inhibition of 5-HT$_4$ receptor-binding of the quinolinecarboxylic acid derivatives of the present invention was examined according to the method described in GROSSMAN et al., Br. J. Pharmacol., 109, 618 (1993).

Method

1. Membrane preparation (5-HT$_4$ receptor)

The longitudinal muscle strip from guinea pig was homogenized in 0.32M sucrose with a Teflon-glass homogenizer. After centrifugation at 900 G for 10 minutes, the upper fraction of lipids and precipitates was discarded and the supernatant was centrifuged at 100.000 G (48,000 rpm) for an hour. The pellet was resuspended in 50 mM HEPES buffer. After incubation at 37° C. for 30 minutes, the suspension was centrifuged at 48,000 rpm for 20 minutes. The pellet was suspended in HEPES buffer supplemented with 10$^{-6}$M pargyline and 0.1% ascorbic acid. The suspension was used for the binding assay.

2. Assay for the inhibition of 5-HT4 receptor-binding

The membrane preparation was incubated at 25° C. for 30 minutes, together with 0.1 nM of [$^3$H]GR113808 (Amersham, selective 5-HT$_4$ receptor binding agent) and the sample compound at the final concentration of 1.0 ml in the sample compound. Non-specific binding was defined as that taken in the presence of 3×10$^{-5}$M 5-HT. B/F separation was performed through GF/B filter treated with 0.1% polyethyleneimine, using a cell harvester. Washing was performed once.

3. Compounds assayed

Each of the sample compounds and cisapride were dissolved in DMSO and each solution was provided for the assay at the final concentration of 1% DMSO.

Results

The IC$_{50}$, value of 50% inhibition, of each of the sample compounds and cisapride in the binding inhibition assay was determined in accordance with the computer program of IC$_{50}$ instructed by Windows-origin (Microcal Software).

The results are shown in Table 3.

TABLE 3

Inhibition of 5-HT$_4$ receptor-binding ([$^3$H]GR113808 binding in guinea pig)

|  |  | Ileum (n = 3) IC$_{50}$ (nM) |
|---|---|---|
| This Invention: |  |  |
| Compound | 5 | 42.19 ± 6.29 |
|  | 20 | 78.14 ± 14.52 |
|  | 11 | 68.70 ± 7.32 |
|  | 10 | 78.50 ± 14.63 |
| Comparison: |  |  |
| Cisapride |  | 97.47 ± 9.17 |

As is noted from the results shown in Table 3, the quinolinecarboxylic acid derivatives of the present invention exhibit a potent activity for inhibiting binding to 5-HT$_4$ receptor in the longitudinal muscular strip of guinea pig ileum.

Experiment 3
Selectivity for receptors

The selectivity for receptors of the quinolinecarboxylic acid derivatives of the present invention was examined by the following method.

Method

1) Dopamine 2 receptor

The affinity to dopamine 2 (D$_2$) receptor was examined according to the method described in MALMBERG, A. et al., Mol Pharmacol., 43, 749–754 (1993).

The affinity for D$_2$ receptor was studied in terms of the inhibition of [$^3$H] raclopride (Daiichi Kagaku Yakuhin Co.) binding to rat striatal membrane. The rat striatum was homogenized in 50 mM Tris hydrochloride buffer (pH 7.4) followed by centrifugation at 48,000 G. The pellet was washed once with Tris hydrochloride buffer. Then the pellet was suspended in 50 mM Tris hydrochloride buffer (containing 120 mM NaCl, 5 mM KCl, 2 mM CaCl$_2$, 1 mM MgCl$_2$, pH 7.4) and provided for use as the membrane preparation. The membrane preparation (0.5 mg protein/ml) was reacted with 1 nM [3H] raclopride at 25° C. for 60 minutes. After the reaction, the membrane was caught by a harvester. Non-specific binding was defined as that taken in the presence of 10 μM haloperidol.

2) Serotonin 3 receptor

The affinity for serotonin 3 receptor was examined by the method described in KILPATRICK, G. J. et al., Nature (London), 330, 746–748 (1987).

The affinity to serotonin 3 (5-HT$_3$) was examined in terms of inhibition of [$^3$H]GR65630 binding (Daiichi Kagaku Yakuhin Co.) binding to rat cerebral cortex membrane. The rat cerebral cortex was homogenized in 50 mM Tris hydrochloride buffer (pH 7.4) followed by centrifugation at 48,000 G. The precipitates were washed once with Tris hydrochloride buffer. Then the precipitates were suspended in 50 mM Tris hydrochloride buffer and provided for use as the membrane preparation. The membrane preparation was reacted with 0.2 nM [$^3$H]GR65630 at 37° C. for 30 minutes. After the reaction, the membrane was caught by a harvester.

Non-specific binding was defined as the binding taken in the presence of 1 μM zacopride.

3) Serotonin $_{1A}$ receptor

The affinity to serotonin $_{1A}$ (5-HT$_{1A}$) receptor was examined by the method described in SCHLEGEL, J. R. et al., Biochem. Pharmacol., 12, 1943–1949 (1986).

The affinity to serotonin $_{1A}$ (5-HT$_{1A}$) was examined in terms of inhibition of [$^3$H] 8-OH-DPAT (Daiichi Kagaku Yakuhin Co.) binding to rat cerebral cortex membrane. The rat cerebral cortex was homogenized in 50 mM Tris hydrochloride buffer (pH 7.4) followed by centrifugation at 48,000 G.

The pellet was washed once with Tris hydrochloride buffer. Then the pellet was suspended in 50 mM Tris hydrochloride buffer (supplemented with 0.01 mM pargyline and 0.1% ascorbic acid, pH 7.7) and provided for use as the membrane preparation. The membrane specimen was reacted with 1 nM [$^3$H] 8-OH-DPAT at 37° C. for 15 minutes. After the reaction, the membrane was caught by a harvester. Non-specific binding was defined as that taken in the presence of 10 μM 5-HT.

4) Compounds assayed

Each of the sample compounds and cisapride were dissolved in DMSO and each solution was provided for the assay at the final concentration of 1% DMSO.

Results

The IC$_{50}$ value of each of the sample compounds and cisapride in the binding inhibition assay was determined in accordance with the computer program of IC50 instructed by Windows-origin.

The results are shown in Table 4.

TABLE 4

| | Selectivity for receptors | | | | |
|---|---|---|---|---|---|
| | Compound of This Invention | | | | Comparison |
| | 5 | 10 | 11 | 20 | Cisapride |
| Dopamine D$_2$ receptor antagonizing action (IC$_{50}$, nM) | — | — | — | — | 107.5 |
| 5-HT$_3$ receptor antagonizing action (IC$_{50}$, nM) | 977 | 811 | 423 | 509 | 97.7 |
| 5-HT$_{1A}$ receptor antagonizing action (IC$_{50}$, nM) | — | — | — | — | 64.7 |

—: no activity in 10 μM

The results shown in Table 4 reveal that the quinolinecarboxylic acid derivatives of the present invention do not show any substantial antagonizing activity for any of dopamine D$_2$ receptor, 5-HT$_3$ receptor and 5-HT$_{1A}$ receptor.

Experiment 4

Gastrointestinal motor activity

The gastrointestinal motor-enhancing activity by the quinolinecarboxylic acid derivatives of the present invention was examined by a modification of the method described in YOSHIDA, N. and ITO, T., The Journal of Pharmacology and Experimental Therapeutics, 257, 781–787 (1991): "AS-4370, a new gastrokinetic agent, enhances upper gastrointestinal motor activity in conscious dogs".

Method

Model dog was prepared and the assay was performed, by a modification of the method by Yoshida et al. For the assay, female beagle dog was used. The animal was anesthetized with pentobarbital (30 mg/kg, i.v.) and the abdominal cavity was opened. Extraluminal force transducers (sensor to measure contraction; Star Medical Co., Model F-12IS) were sutured onto five (5) sites, i.e., the gastric antrum, 3 cm proximal to the pyloric ring, the duodenum, 5 cm distal to the pyloric ring, the jejunum, 70 cm distal to the pyloric ring, the ileum, 5 cm proximal to the ileum-colon junction, and the colon, 5 cm distal to the ileum-colon junction. The lead wires of these force transducers were taken out of the abdominal cavity and then brought out through a skin incision made between the scapulae, at which a connector was connected. After the operation, a jacket protector was placed on the dog to protect the connector. Measurement of the gastrointestinal motor activity started from two weeks after the operation. For ad libitum measurement, a telemeter (electrowave data transmitter; Star Medical Co., Model DAT-80T) was connected with the connector to determine the contractive motility at each site of the gastrointestinal tract. The data was stored in a computer (NEC, Model PC9801FA) via a telemeter (receiver; Star Medical Co., Model DAT-80A) for analysis.

The drug (vehicle, cisapride and Compound 5 of the present invention) was administered intravenously through the forepaw two hours after feeding (1116 kcal; Oriental Yeast Co.).

Cisapride and Compound 5 of the present invention were dissolved in 0.5% dl-lactate solution, respectively. For control, 0.5% dl-lactate solution was employed as the vehicle.

Results

The gastrointestinal motility was processed by the computer every 15 minutes in terms of motility index (M.I., g-min). The motor index given by the processing system corresponded to the area surrounded by the contraction wave and base line drawn by the computer on the display. Software for analysis: Software for analysis of organ motility ESC-820, Star Medical Co.).

With respect to the gastric antrum, the duodenum and the jejunum, M.I. is expressed by the mean value of the motility index for the 15-minute period for the enhancing activity of motility before and 1 hour after administration, i.e., (total sum of M.I. (%) between 0 and 1 hour)/4. With respect to the ileum and the colon, M.I. is expressed by the mean value for the 15-minute period for the enhancing activity of motility before and 0.5 hour after administration, i.e., (total sum of M.I. (%) between 0 and 0.5 hour)/2. In this case, M.I. (%) was calculated by designating as 100% the mean value for the 15-minute period 30 minutes before administration.

The results are shown in FIG. 1. As is evident from FIG. 1, the quinolinecarboxylic acid derivative of the present invention showed a potent activity particularly on the motility in the gastric antrum and the ileum.

Industrial Applicability

The quinolinecarboxylic acid derivative or its pharmaceutically acceptable salt of the present invention acts on a serotonin 4 receptor and thereby showing a serotonin-like stimulating activity on serotonin 4 receptor. More specifically, the compounds of the present invention exhibit an action of enhancing the gastrointestinal motor functions to improve the gastrointestinal conditions such as heartburn, anorexia, bowel pain, abdominal distension, etc., accompanied by chronic gastritis, diabetes mellitus or postoperative gastro-paresis, and are thus effective for the treatment of gastro-esophagal reflux, intestinal pseudo-obstruction and constipation.

We claim:

1. A quniolinecarboxylic acid derivative represented by formula (A):

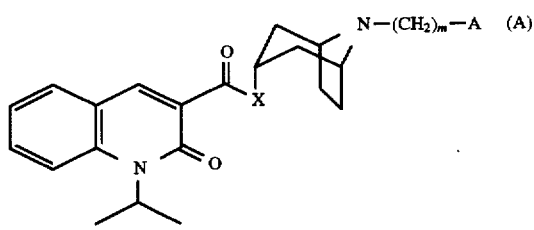

wherein:

X represents an oxygen atom or imino group;

m represents 0 or an integer of 1 to 6;
and,

A represents an alkenyl group having 2–6 carbon atoms, an alkynyl group having 2–6 carbon atoms, a haloalkyl group having 1 to 3 carbon atoms, hydroxy group, an alkoxy group having 1–6 carbon atoms, an acyloxy group having 2–8 carbon atoms, an alkoxyalkoxy group having 2–8 carbon atoms, a mono- or di-alkylamino group having 1–6 carbon atoms, an alkythio group having 1–6 carbon atoms, an alkylsulfinyl group having 1–6 carbon atoms, an alkylsulfonyl group having 1–6 carbon atoms, a phenylsulphonyl group, tolylsulfonyl group or naphthylsulfonyl group, a phenoxy group, tolyloxy group or naphthyloxy group, morpholinyl group, piperidyl group, tetrahydropyranyl group, an alkoxycarbonyl group having 2–7 carbon atoms, carboxyl group, an alkanoyl group having 2–8 carbons atoms, cyano group or carbamoyl group; or a pharmaceutically acceptable salt thereof.

2. A quinolinecarboxylic acid derivative or a pharmaceutically acceptable salt thereof according to claim 1, which is represented by formula (B):

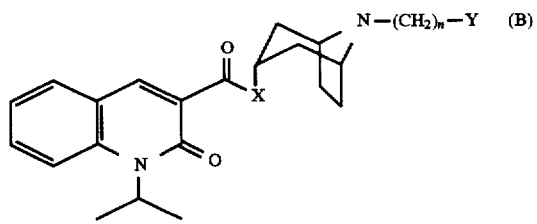

wherein X represents an oxygen atom or imino group; n represents an integer of 1 to 6; and Y represents hydroxy group, an alkoxy group having 1–6 carbon atoms, an alkanoyl group having 2–8 carbon atoms, an alkoxycarbonyl group having 2–7 carbon atoms or morpholinyl group.

3. A quniolinecarboxylic acid derivative or a pharmaceutically acceptable salt thereof according to claim 1, which is represented by formula (C):

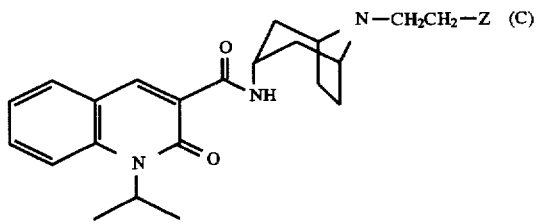

wherein Z represents hydroxymethyl, methoxy, ethoxy or morpholino group.

4. A pharmaceutical composition comprising as an effective ingredient a quinolinecarboxylic acid derivative or pharmaceutically acceptable salt thereof according to claim 1 and a pharmaceutically acceptable carrier, wherein said effective ingredient is added in an amount effective for stimulating a serotonin 4 receptor.

5. A method for stimulating a serotonin 4 receptor which comprises administering to human an effective dose of a quinolinecarboxylic acid derivative or a pharmaceutically acceptable salt thereof according to claim 1.

6. The quinolinecarboxylic acid derivative or a pharmaceutically acceptable salt thereof according to claim 1, which is endo-N-(8-(3-hydroxypropyl)-8-azabicyclo[3.2.1] oct-3-yl)-1-isopropyl-2-oxo-1,2-dihydro-3-quinolinecarboxamide.

* * * * *